United States Patent [19]

Amoo et al.

[11] Patent Number: 5,633,271

[45] Date of Patent: May 27, 1997

[54] ARTHROPODICIDAL OXAZOLINES AND THIAZOLINES

[75] Inventors: Victor E. Amoo; George P. Lahm, both of Wilmington; Thomas M. Stevenson, Newark, all of Del.

[73] Assignee: E. I. Du Pont de Nemours and Company, Wilmington, Del.

[21] Appl. No.: 585,970

[22] Filed: Jan. 16, 1996

Related U.S. Application Data

[63] Continuation-in-part of Ser. No. 338,500, Nov. 22, 1994, abandoned, which is a continuation of Ser. No. 24,576, Mar. 1, 1993, abandoned, which is a continuation of Ser. No. 956,927, Oct. 5, 1992, abandoned, which is a continuation of Ser. No. 889,026, May 26, 1992, abandoned.

[51] Int. Cl.⁶ .......................... A61K 31/42; A61K 3/425; C07D 263/10; C07D 277/10
[52] U.S. Cl. .......................... 514/365; 514/374; 548/146; 548/237
[58] Field of Search .................. 548/146, 237; 514/365, 374

[56] References Cited

U.S. PATENT DOCUMENTS 4,889,867 12/1989 Lutomski et al. ................ 514/365
4,977,171 12/1990 Suzuki et al. .................... 514/365
5,141,948 8/1992 Miyamoto et al. ............... 514/365

FOREIGN PATENT DOCUMENTS 0345775 12/1989 European Pat. Off. ...... C07D 263/10
0432661 6/1991 European Pat. Off. ...... C07D 263/12

OTHER PUBLICATIONS

Ardabilchi, N. et al, *JCS Perkins I*, 539–543 (1979).
Miyamoto, S. et al, *Chemical Abstracts*, 117(13), p. 745, Abstract No. 131181s, Sep. 1992.
Miyamoto, S. et al, *Chemical Abstracts*, 118(23), p. 393, Abstract No. 228265f Jun. 1993.

*Primary Examiner*—Robert Gerstl

[57] ABSTRACT

Arthropodicidally active compounds, compositions and a method for using them, the compounds having the formula

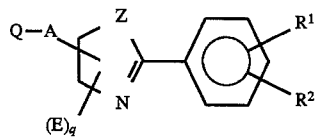

wherein A, Q, Z, $(E)_q$, $R^1$ and $R^2$ are as defined in the text.

11 Claims, No Drawings

ARTHROPODICIDAL OXAZOLINES AND THIAZOLINES

CROSS-REFERENCE TO RELATED APPLICATIONS

This application is a continuation in part of application Ser. No. 08/338,500 filed Nov. 22, 1994, now abandoned which is a continuation of application Ser. No. 08/024,576 filed Mar. 1, 1993, now abandoned, which is a continuation of application Ser. No. 07/956,927 filed Oct. 5, 1992, now abandoned which is a continuation of application Ser. No. 07/889,026 filed May 26, 1992 now abandoned.

BACKGROUND OF THE INVENTION

The arthropodicidal and acaricidal oxazolines and thiazolines of this invention are characterized by a fused ring system or a monocyclic heterocycle. This ring distinguishes the compounds of this invention from those of EP 345,775 and EP 432,661. N. Ardabilchi, et al., *J. Chem. Soc, Perkin Trans I* (1979), 539–543 discloses 4,5-dihydro-4-methyl-5-(1-naphthalenyl)-2-phenyloxazole but does not disclose any arthropodicidal utility.

SUMMARY OF THE INVENTION

The invention pertains to compounds of Formula I, including all geometric and stereoisomers, agriculturally suitable salts thereof, agricultural compositions containing them and their use as arthropodicides and acaricides in both agronomic and nonagronomic environments. The compounds are

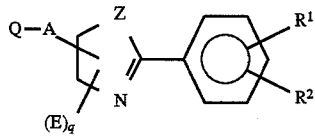

I wherein:

A is selected from the group a direct bond and $C_1$-$C_3$ straight or branched chain alkylene;

E is selected from the group $C_1$-$C_4$ alkyl and $C_1$-$C_4$ haloalkyl;

Z is selected from the group O and S;

q is 0, 1, 2 or 3;

Q is a 5- to 16- membered aromatic ring system selected from the group:
- (i) monocyclic aromatic ring containing 1 to 4 heteroatoms independently selected from the group 0–4 nitrogen, 0–1 oxygen, and 0–1 sulfur; p2 (ii) fused carbobicyclic ring containing 8 to 12 carbons, with the proviso that when the ring is naphthyl and is on the oxazoline ring carbon adjacent to the oxazoline ring oxygen, and when E is $CH_3$ and q is 1, then $R^1$ is other than H;
- (iii) fused carbotricyclic ring containing 12 to 16 carbons;
- (iv) fused bicyclic ring containing 1 to 4 heteroatoms independently selected from the group 0–4 nitrogen, 0–2 oxygen, and 0–2 sulfur;
- (v) fused tricyclic ring containing 1 to 6 heteroatoms independently selected from the group 0–4 nitrogen, 0–2 oxygen, and 0–2 sulfur; and
- (vi) phenyl substituted with M-$J^1$;

Q being substituted with 1 to 6 substituents selected independently from the group $R^3$, $R^4$, $(R^5)_p$ and $(R^6)_m$;

$R^1$ and $R^2$ are independently selected from the group H, halogen, $C_1$-$C_6$ alkyl, $C_1$-$C_6$ haloalkyl, $C_1$-$C_6$ haloalkoxy, $C_{1-C6}$ alkylthio, CN and $NO_2$;

$R^3$ and $R^5$ are independently selected from the group H, halogen, $C_1$-$C_{16}$ alkyl, $C_1$-$C_{16}$ haloalkyl, $C_3$-$C_7$ cycloalkyl, $C_4$-$C_{16}$ cycloalkylalkyl, $C_2$-$C_{16}$ alkenyl, $C_2$-$C_{16}$ haloalkenyl, $C_2$-$C_{16}$ alkynyl, $C_2$-$C_{16}$ haloalkynyl, $C_2$-$C_{16}$ alkoxyalkoxy, $OR^7$, $R^7OC(O)$—, $R_7C(O)$—, $Si(R^{13})(R^{14})R^{15}$ and M-J;

$R^4$ is selected from the group H, halogen, $C_1$-$C_6$ alkyl, $C_1$-$C_6$ alkoxy, $C_1$-$C_6$ haloalkyl and $C_1$-$C_6$ haloalkoxy;

$R^6$ is selected from the group H, halogen, $C_1$-$C_{10}$ alkyl, $C_1$-$C_6$ alkoxy, $C_1$-$C_6$ haloalkyl, $C_1$-$C_6$ haloalkoxy; and phenyl optionally substituted with $R^8$;

$R^7$ is selected from the group $C_3$-$C_7$ cycloalkyl, $C_4$-$C_7$ cycloalkylalkyl, $C_1$-$C_{16}$ alkyl, $C_1$-$C_{16}$ haloalkyl, $C_2$-$C_{16}$ alkenyl, $C_2$-$C_{16}$ haloalkenyl, $C_2$-$C_{16}$ alkynyl and $C_2$-$C_{16}$ haloalkynyl;

$R^8$ is selected from the group halogen, $C_1$-$C_6$ alkyl, $C_1$-$C_6$ alkoxy, $C_1$-$C_6$ haloalkyl, $C_1$-$C_6$ haloalkoxy and $Si(R^9)(R^{10})R^{11}$;

$R^9$, $R^{10}$ and $R^{11}$ are independently $C_1$-$C_{12}$ alkyl;

M is selected from the group a direct bond, S, O, C(=O), C(=O)O—$C_1$-$C_2$ alkylene, $C_1$-$C_4$ alkylene, O—$C_1$-$C_4$ alkylene and O—$C_2$-$C_4$ alkenylene, wherein when M is O—$C_1$-$C_4$ alkylene or O—$C_2$-$C_4$ alkenylene, the oxygen atom is attached to either ring and when M is C(=O)O—$C_1$-$C_2$, the C(=O) is attached to either ring;

J is selected from the group phenyl optionally substituted with independently selected substituents $(R^{12})_n$; and a 5-or 6-membered aromatic ring, attached through carbon or nitrogen, containing 1 to 4 heteroatoms independently selected from the group 0–4 nitrogen, 0–1 oxygen, and 0–1 sulfur, the ring optionally substituted with independently selected substituents $(R^{12})_n$;

$J^1$ is selected from the group a 5- membered aromatic ring, attached through carbon or nitrogen, containing 1 to 4 heteroatoms independently selected from the group 0–4 nitrogen, 0–1 oxygen, and 0–1 sulfur, and a 6-membered ring containing 2 to 4 nitrogen atoms each ring optionally substituted with independently selected substituents $(R^{12})_n$;

$R^{12}$ is selected from the group halogen, $C_1$-$C_6$ alkyl, $C_1$-$C_6$ alkoxy, $C_1$-$C_6$ haloalkyl, $C_1$-$C_6$ haloalkoxy and $Si(R^{13})(R^{14})R^{15}$;

$R^{13}$, $R^{14}$ and $R^{15}$ are independently $C_1$-$C_{12}$ alkyl;

m and n are integers independently selected from 1 to 4; and p is 1 or 2.

Preferred Compounds A are compounds of Formula I wherein Q is selected from the group:

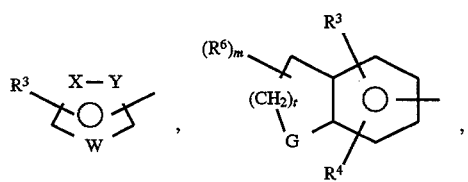

Q-1     Q-2

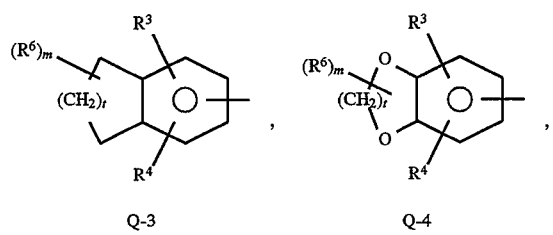

Q-3, Q-4

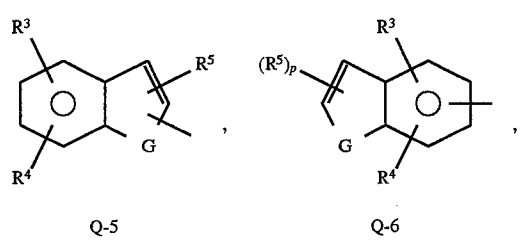

Q-5, Q-6

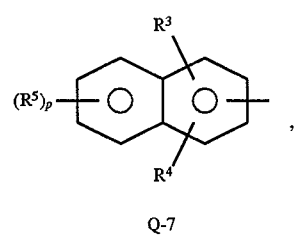

Q-7

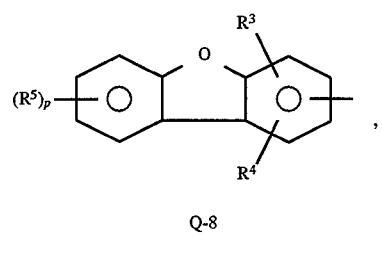

Q-8

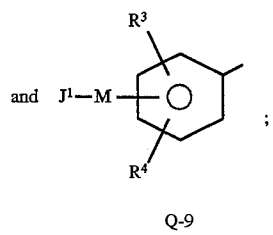

Q-9

G being selected from the group O and S;

W, X and Y being independently selected from the group N, S, O, $CR^5$, $N=CR^6$ and $NR^{16}$ wherein only one of W, X and Y is O, S or $N=CR^6$;

$R^{16}$ being selected from the group H, $C_1-C_6$ alkyl and phenyl optionally substituted with 1 to 3 substituents independently selected from the group $R^{17}$;

$R^{17}$ is selected from the group $C_1-C_3$ alkyl, $C_1-C_3$ haloalkyl, halogen, $NO_2$ and CN; and t is 1, 2 or 3.

Preferred compounds of this invention are those wherein Q is selected from the group

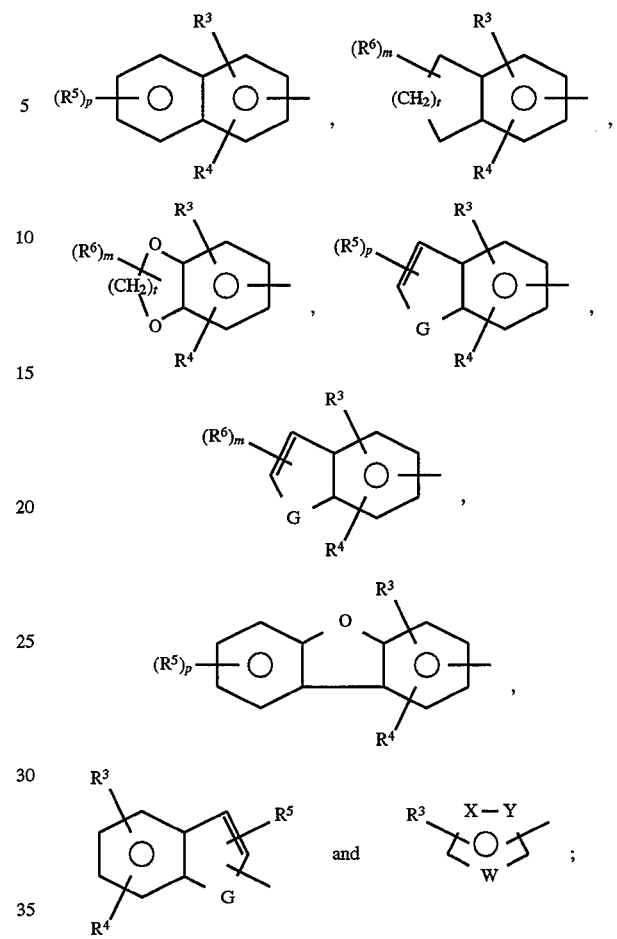

A is selected from the group a direct bond and $C_1-C_3$ straight or branched chain alkylene;

G and Z are independently selected from the group O and S;

W, X and Y are independently selected from the group S, O, $CR^3$, $N=CR^7$ and $NR^8$ wherein only one of W, X and Y can be O, S or $N=CR^7$;

$R^1$ and $R^2$ are independently selected from the group H, halogen, $C_1-C_6$ alkyl, $C_1-C_6$ haloalkyl, $C_1-C_6$ haloalkoxy, $C_1-C_6$ alkylthio, CN and $NO_2$;

$R^3$ and $R^5$ are independently selected from the group H, halogen, $C_1-C_{16}$ alkyl, $C_3-C_7$ cycloalkyl, $C_4-C_{16}$ cycloalkylalkyl, $C_1-C_{16}$ haloalkyl, $C_2-C_{16}$ alkenyl, $C_2-C_{16}$ haloalkenyl, $C_2-C_{16}$ alkynyl, $C_2-C_{16}$ haloalkynyl, $C_2-C_{16}$ alkoxyalkoxy, $OR^9$, $R^9OC(O)—$, $R^9C(O)—$ and

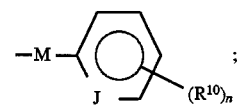

$R^4$ and $R^7$ are independently selected from the group H, halogen, $C_1-C_6$ alkyl, $C_1-C_6$ alkoxy, $C_1-C_6$ haloalkyl and $C_1-C_6$ haloalkoxy;

$R^6$ is selected from the group H, halogen, $C_1-C_{10}$ alkyl and phenyl optionally substituted with $R^{10}$;

$R^8$ is selected from the group H and $C_1-C_6$ alkyl;

$R^9$ is selected from the group $C_3-C_7$ cycloalkyl, $C_4-C_7$ cycloalkylalkyl, $C_1-C_{16}$ alkyl, $C_1-C_{16}$ haloalkyl, $C_2-C_{16}$ alkenyl, $C_2-C_{16}$ haloalkenyl, $C_2-C_{16}$ alkynyl and $C_2-C_{16}$ haloalkynyl;

$R^{10}$ is selected from the group halogen, $C_1-C_6$ alkyl, $C_1-C_6$ alkoxy, $C_1-C_6$ haloalkyl, $C_1-C_6$ haloalkoxy and $Si(R^{11})(R^{12})R^{13}$;

$R^{11}$, $R^{12}$ and $R^{13}$ are independently $C_1-C_3$ alkyl;

J is selected from the group CH, $CR^{10}$ and N;

M is selected from the group a direct bond, O, C(O), C(O)O and $C_1-C_3$ straight or branched chain alkylene;

m is an integer from 1 to 4;

n is 0 or an integer from 1 to 4;

p is 1 or 2;

t is 1, 2 or 3; and q is 0.

Preferred Compounds B are Compounds A wherein where one of W, X or Y is S, the remaining two are not both $CR^5$.

Preferred Compounds C are Compounds A wherein:

A is a direct bond;

$R^1$ is selected from the group F and Cl in the 2-position;

$R^2$ is selected from the group H, F and Cl in the 6-position;

$R^3$ and $R^5$ are independently selected from the group H, halogen, $C_1-C_6$ alkyl, $C_1-C_6$ alkoxy, $C_1-C_6$ haloalkyl, $C_1-C_6$ haloalkoxy and M-J; and J is selected from the group phenyl, thienyl, pyridyl and furyl.

Preferred Compounds D are Compounds C wherein Q is selected from the group Q-1, Q-2, Q-3 and Q-4.

Preferred Compounds E are Compounds D wherein:

Q is Q-1;

W is S;

X and Y are $CR^5$;

$R^3$ is M-J;

M is a direct bond;

J is phenyl;

$R^{12}$ is in the meta or para position and is selected from the group halogen and $CF_3$; and n is 1 or 2.

Preferred Compound F is the compound of Preferred D which is:

(2-(2,6-difluorophenyl)-4-[5-(1,1-dimethylethyl)-2-thienyl]-4,5-dihydrooxazole.

Preferred Compound G is the compound of Preferred D which is:

2-(2,6-difluorophenyl)-4-(2,2-dimethyl-1,3-benzodioxol-5-yl)-4,5-dihydrooxazole.

Preferred Compound H is the compound of Preferred E which is:

4-[5-(4-chlorophenyl)-2-thienyl]-2-2-(2,6-difluorophenyl)-4,5-dihydrooxazole.

The invention also pertains to a method for controlling arthropods comprising applying to the arthropods or their environment an arthropodicidally effective amount of a compound of Formula IA

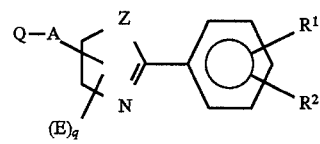

wherein:

A is selected from the group a direct bond and $C_1-C_3$ straight or branched chain alkylene;

E is selected from the group $C_1-C_4$ alkyl and $C_1-C_4$ haloalkyl;

Z is selected from the group O and S;

q is 0, 1, 2 or 3;

Q is a 5- to 16- membered aromatic ring system selected from the group:
  (i) monocylic aromatic ring containing 1 to 4 heteroatoms independently selected from the group 0–4 nitrogen, 0–1 oxygen, and 0–1 sulfur;
  (ii) fused carbobicyclic ring containing 8 to 12 carbons;
  (iii) fused carbotricyclic ring containing 12 to 16 carbons;
  (iv) fused bicylic ring containing 1 to 4 heteroatoms independently selected from the group 0–4 nitrogen, 0–2 oxygen, and 0–2 sulfur;
  (v) fused tricylic ring containing 1 to 6 heteroatoms independently selected from the group 0–4 nitrogen, 0–2 oxygen, and 0–2 sulfur; and
  (vi) phenyl substituted with M-$J^1$;

Q being substituted with 1 to 6 substituents selected independently from the group $R^3$, $R^4$, $(R^5)_p$ and $(R^6)_m$;

$R^1$ and $R^2$ are independently selected from the group H, halogen, $C_1-C_6$ alkyl, $C_1-C_6$ haloalkyl, $C_1-C_6$ haloalkoxy, $C_1-C_6$ alkylthio, CN and $NO_2$;

$R^3$ and $R^5$ are independently selected from the group H, halogen, $C_1-C_{16}$ alkyl, $C_1-C_{16}$ haloalkyl, $C_3-C_7$ cycloalkyl, $C_4-C_{16}$ cycloalkylalkyl, $C_2-C_{16}$ alkenyl, $C_2-C_{16}$ haloalkenyl, $C_2-C_{16}$ alkynyl, $C_2-C_{16}$ haloalkynyl, $C_2-C_{16}$ alkoxyalkoxy, $OR^7$, $R^7OC(O)$—, $R^7C(O)$—, $Si(R^{13})(R^{14})R^{15}$ and M-J;

$R^4$ is selected from the group H, halogen, $C_1-C_6$ alkyl, $C_1-C_6$ alkoxy, $C_1-C_6$ haloalkyl and $C_1-C_6$ haloalkoxy;

$R^6$ is selected from the group H, halogen, $C_1-C_{10}$ alkyl, $C_1-C_6$ alkoxy, $C_1-C_6$ haloalkyl, $C_1-C_6$ haloalkoxy; and phenyl optionally substituted with $R^8$;

$R^7$ is selected from the group $C_3-C_7$ cycloalkyl, $C_4-C_7$ cycloalkylalkyl, $C_1-C_{16}$ alkyl, $C_1-C_{16}$ haloalkyl, $C_2-C_{16}$ alkenyl, $C_2-C_{16}$ haloalkenyl, $C_2-C_{16}$ alkynyl and $C_2-C_{16}$ haloalkynyl;

$R^8$ is selected from the group halogen, $C_1-C_6$ alkyl, $C_1-C_6$ alkoxy, $C_1-C_6$ haloalkyl, $C_1-C_6$ haloalkoxy and $Si(R^9)(R^{10})R^{11}$;

$R^9$, $R^{10}$ and $R^{11}$ are independently $C_1-C_{12}$ alkyl;

M is selected from the group a direct bond, S, O, C(=O), C(=O)O—$C_1-C_2$ alkylene, $C_1-C_4$ alkylene, O—$C_1-C_4$ alkylene and O—$C_2-C_4$ alkenylene, wherein when M is O—$C_1-C_4$ alkylene or O—$C_2-C_4$ alkenylene, the oxygen atom is attached to either ring and when M is C(=O)O—$C_1-C_2$, the C(=O) is attached to either ring;

J is selected from the group phenyl optionally substituted with independently selected substituents $(R^{12})_n$; and a 5-or 6-membered aromatic ring, attached through carbon or nitrogen, containing 1 to 4 heteroatoms independently selected from the group 0–4 nitrogen, 0–1 oxygen, and 0–1 sulfur, the ring optionally substituted with independently selected substituents $(R^{12})_n$;

$J^1$ is selected from the group a 5- membered aromatic ring, attached through carbon or nitrogen, containing 1 to 4 heteroatoms independently selected from the group 0–4 nitrogen, 0–1 oxygen, and 0–1 sulfur, and a 6-membered ring containing 2 to 4 nitrogen atoms each ring optionally substituted with independently selected substituents $(R^{12})_n$;

$R^{12}$ is selected from the group halogen, $C_1$–$C_6$ alkyl, $C_1$–$C_6$ alkoxy, $C_1$–$C_6$ haloalkyl, $C_1$–$C_6$ haloalkoxy and $Si(R^{13})(R^{14})R^{15}$;

$R^{13}$, $R^{14}$ and $R^{15}$ are independently $C_1$–$C_{12}$ alkyl;

m and n are integers independently selected from 1 to 4; and p is 1 or 2.

Compounds of this invention can exist as one or more stereoisomers. The various stereoisomers include enantiomers, diastereomers and geometric isomers. One skilled in the art will appreciate that one stereoisomer may be more active than the others and how to separate stereoisomers. Accordingly, the present invention comprises racemic mixtures, individual stereoisomers, and optically active mixtures of compounds of Formula I as well as agriculturally suitable salts thereof.

The term "aromatic ring system" is defined as those ring systems which satisfy the Hackel rule, examples include: (i) a 5- or 6- membered monocyclic aromatic ring containing 1 to 4 heteroatoms such as furyl, furazanyl, thienyl, pyrrolyl, pyrazolyl, oxazolyl, oxadiazolyl, imidazolyl, isoxazolyl, thiazolyl, thiadiazolyl isothiazolyl, tetrazolyl, pyridyl, pyrimidinyl, pyridazinyl, pyrazinyl and triazinyl with said ring attached through any available carbon or nitrogen, for example, when the aromatic ring system is furyl, it can be 2-furyl or 3-furyl, for pyrrolyl, the aromatic ring system is 1-pyrrolyl, 2-pyrrolyl or 3-pyrrolyl, for pyridyl, the aromatic ring system is 2-pyridyl, 3-pyridyl or 4-pyridyl and similarly for other monocyclic aromatic rings; (ii) fused carbobicyclic ring containing at least one phenyl ring, examples include naphthyl and tetralinyl; (iii) fused carbotricylic ring containing at least one phenyl ring, examples include fluorenyl and phenanthrenyl; (iv) fused bicyclic rings containing 1 to 4 heteroatoms and 1 or 2 aromatic rings, examples include quinolyl, isoquinolyl, quinoxalinyl, benzofuryl, isobenzofuranyl, benzothienyl, benzodioxolyl, chromanyl, indolinyl, isoindolyl, thienofuranyl, and purinyl; and (v) fused tricyclic rings containing 1 to 6 heteroatoms and at least 1 aromatic ring, examples include acridinyl, phenanthridinyl, phenanthrolinyl, phenoxazinyl, and dibenzofuranyl. As with the monocyclic aromatic rings, the bicyclic and tricyclic aromatic ring systems can be attached through any available carbon or nitrogen, for example, for naphthyl, the carbobicyclic aromatic ring system is 1-naphthyl or 2-naphthyl, for benzofuryl, the aromatic ring system can be ,2-, 3-, 4-, 5-, 6-, or 7-benzofuryl, for fluorenyl, the aromatic ring system can be 1-, 2-, 3-, 4-, or 9-fluorenyl and similarly for the other bicyclic and tricyclic aromatic ring systems. Q-1 is an example of aromatic ring system (i); Q-3 and Q-7 of ring system (ii); Q-2, Q-4, Q-5 and Q-6 of ring system (iv); Q-8 of ring system (v); and Q-9 of ring system (vi).

In the above recitations, the term "alkyl" used either alone or in compound words such as "alkylthio" or "haloalkyl", denotes straight or branched alkyl such as methyl, ethyl, n-propyl, isopropyl and the different butyl, pentyl and hexyl isomers. Alkylene and alkenylene denote both straight and branch chains.

Alkoxy denotes methoxy, ethoxy, n-propyloxy, isopropyloxy and the different butoxy, pentoxy and hexyloxy isomers. Alkenyl denotes straight or branched chain alkenes such as vinyl, 1-propenyl, 2-propenyl and the different butenyl, pentenyl and hexenyl isomers. Alkynyl denotes straight chain or branched alkynes such as ethynyl, 1-propynyl, 3-propynyl and the different butynyl, pentynyl and hexynyl isomers. Cycloalkyl denotes cyclopropyl, cyclobutyl, cyclopentyl and cyclohexyl. The term "halogen", either alone or in compound word such as "haloalkyl", denotes fluorine, chlorine, bromine or iodine. Further, when used in compound words such as "haloalkyl", said alkyl can be partially or fully substituted with independently selected halogen atoms. Examples of haloalkyl include $CH_2CH_2F$, $CF_2CF_3$ and $CH_2CHFCl$. The terms "haloalkenyl" and "haloalkynyl" are defined analogously to the term "haloalkyl".

The total number of carbon atoms in a substituent group is indicated by the "$C_i$–$C_j$" prefix where i and j are numbers from 1 to 16. For example, $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$.

When a compound is substituted with a substituent bearing a subscript that indicates the number of said substituents can exceed 1, said substituents (when they exceed 1) are independently selected from the group of defined substituents.

DETAILS OF THE INVENTION

Compounds of Formula I can be made from amino alcohols (or thiols) of Formula II and benzoic acid derivatives as shown in Scheme 1. The transformation generally consists of two steps. First, the compound of Formula II is condensed with the benzoic acid derivative to form an amide of Formula III. A generally useful way to do this is to treat the compound of Formula II with an aroyl chloride in the presence of an acid acceptor (usually a tertiary amine base such as triethylamine) at room temperature or below. This reaction can be carried out in an inert solvent such as dichloromethane, tetrahydrofuran, toluene, and other solvents that will not react with acid chlorides or bases. There are other useful ways to form amides, many examples of which are found in Larock, "Comprehensive Organic Transformations," VCH Publishers, Inc., New York, pp. 972–981). The second step carried out is the ring closure. This can be accomplished by treating the intermediate amide of Formula III with a dehydrating agent. Some useful reagent systems for this transformation include but are not limited to triphenyl phosphine/carbon tetrachloride, diethylazodicarboxylate/triphenyl phosphine, and thionyl chloride. An especially useful method for ring closure involves treatment of the amide with thionyl chloride in benzene or other inert solvent at reflux until the starting material is consumed. The residue of this reaction is treated with an inorganic base such as sodium or potassium hydroxide in an alcoholic or aqueous medium. Many methods for ring closure to oxazolines have been compiled by Frump (*Chemical Rev.* (1971), 71, 483–505).

Scheme 1

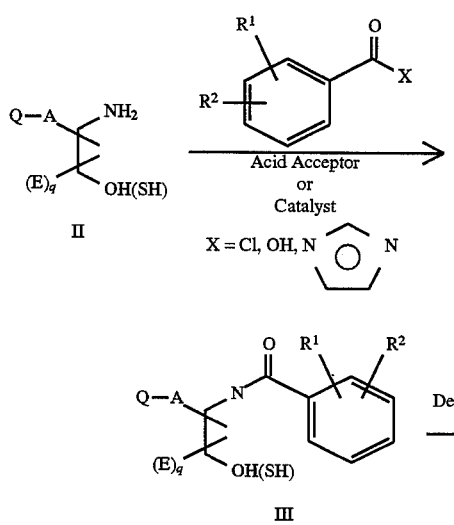

Alternatively, compounds of Formula III (where A is a direct bond) can be prepared in two steps as shown in Scheme 2. First, compounds of Formula IV are amidoalkylated with a compound of Formula V to form Formula VI compounds. A typical reaction involves the combination of compounds of Formulae IV and V in an acid such as sulfuric acid, methanesulfonic acid, trifluoroacetic acid, polyphosphoric acid and perchloric acid. The reaction can be run in a cosolvent such as acetic acid. The reaction temperature can range from −10° to 200° C. with 0°–100° C. being preferred. Alternatively, the reaction can be carried out in an inert solvent such as chloroform, methylene chloride, benzene, toluene and ether in the presence of a Lewis acid such as aluminum chloride or boron trifluoride. Amidoalkylation reactions have been extensively reviewed in the literature (see Zaugg, *Synthesis* (1984), 85–110). The second step is the reduction of a Formula VI compound to form a Formula III compound. Reductions of this type are well-known in the art (see Hudlicky, *Reductions in Organic Chemistry* (1984), 136–163). Typical reducing agents include the alkali metal borohydrides and diborane.

Scheme 2

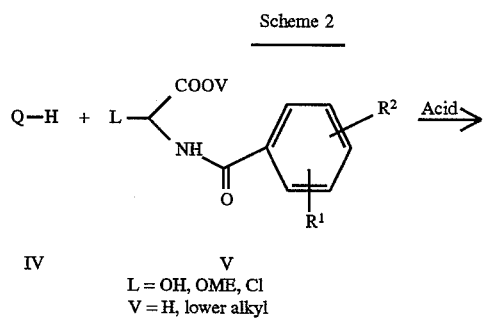

L = OH, OMe, Cl
V = H, lower alkyl

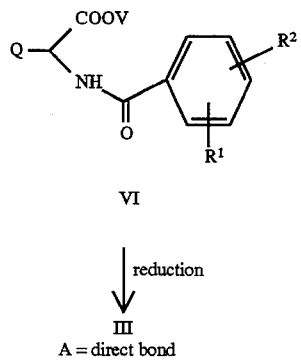

The preparation of Formula V compounds can be accomplished by refluxing glyoxylic acid derivatives (Formula VII) and commercially available benzamides (Formula VIII) in an inert solvent such as acetone, benzene and chloroform (Scheme 3). This procedure is known in the art (see Ben-Ishai, *Tetrahedron* (1975), 31, 863–866 and *Tetrahedron* (1977), 33, 881–883).

Scheme 3

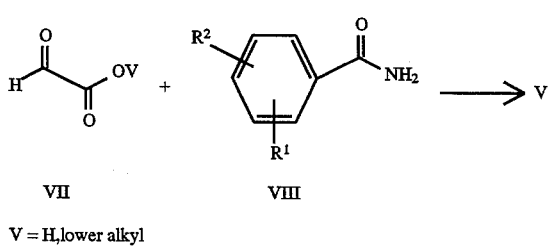

V = H, lower alkyl

As shown in Scheme 4, amino alcohols of Formula II can be produced by the treatment of an amino acid derivative of Formula IX with a reducing agent. In the reduction process, aminoesters are preferred, but amino acids themselves can also be used. There are many reagents known to reduce acids and esters to alcohols. (See Larock, loc. cit., pp. 548–553). Particularly useful are alkali metal hydrides and boranes. For example, treatment of a compound of Formula IX with lithium aluminum hydride at 0°–50° C. in ethereal solvents such as tetrahydrofuran, ether, or dimethoxyethane gives an alcohol of Formula II.

Scheme 4

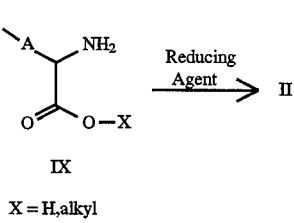

X = H, alkyl

As shown in Scheme 5, amino alcohols of Formula II can be produced by the direct reduction of oximo acids and esters of Formula X with boranes or alkali metal hydrides. The reaction conditions with lithium aluminum hydride are as described for Scheme 4.

Scheme 5

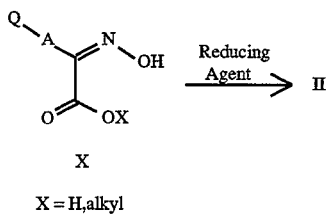

X = H,alkyl

Scheme 8

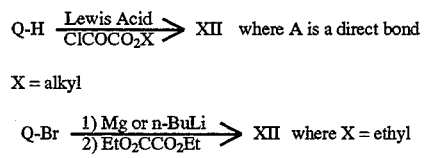

X = alkyl

Aryl-substituted amino acids and esters of Formula IX are known in the art as are methods for their preparation. Useful compendia of methods for their synthesis are contained in Kukolja (*J. Med. Chem.* (1985), 28, 1886–1896), Bohme (*J. Med. Chem.* (1980), 23,405–412), and O'Donnell (*Tetrahedron Lett.* (1989), 30, 3909–3912) and references cited within.

Oximo esters of Formula X are especially suitable intermediates for the synthesis of compounds of Formula I. They can be made from aryl acetic esters of Formula XI by reaction, in the presence of base, with nitrosating agents such as inorganic and organic nitrites as shown in Scheme 6. Typically, the compound of Formula VI is treated with an alkyl nitrite such as butyl nitrite in an alcoholic solvent such as ethanol in the presence of a strong base such as sodium ethoxide at the reflux temperature of the solvent.

Scheme 6

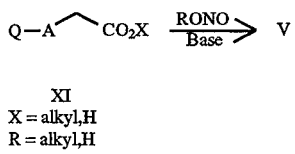

XI
X = alkyl,H
R = alkyl,H

Alternatively, as shown in Scheme 7, compounds of Formula X can be produced from aryl glyoxalates of Formula XII by treatment with a derivative of hydroxylamine. Aryl glyoxalates can be made by the reaction of an organometallic species with a derivative of oxalic acid. For instance, diethyl oxalate can be treated with an aryl Grignard reagent at low temperature in ether/tetrahydrofuran mixtures (Rambaud, et al., *Synthesis* (1988), 564–567).

Scheme 7

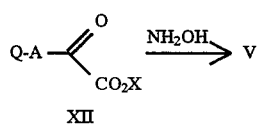

XII

X = H,alkyl

Another method for the synthesis of compounds of Formula XII, shown in Scheme 8, is by use of the Friedel-Crafts reaction. Monoesters of oxalyl chloride react with electron-rich aromatics of Formula XIII in the presence of Lewis acids to give compounds of Formula XII. See Olah ed., "Friedel-Crafts and Related Reactions," Vol. 3, Part 1, pp. 1–16. Treatment of compounds of Formula XIII with aluminum chloride and ethyl or methyloxalyl chloride in an inert solvent such as dichloromethane, nitrobenzene, carbon disulfide, or dichloroethane will produce compounds of Formula XII.

Compounds of the instant invention where Q is phenyl substituted with M-J$^1$ can be made by methods known in the art. As shown in Scheme 9, compounds of Formula XIII substituted by a halogen or triflate can be coupled with heterocyclic compounds of Formula XIV containing tin, zinc, boron, magnesium, lithium, or other metal in the presence of a nickel or palladium catalyst to give compounds of the present invention where M is a direct bond or an alkylene group. Methods and conditions for the specific introduction of heterocyclic compounds under these conditions can be found in Kalinin, *Synthesis*, (1992), 413–432.

Scheme 9

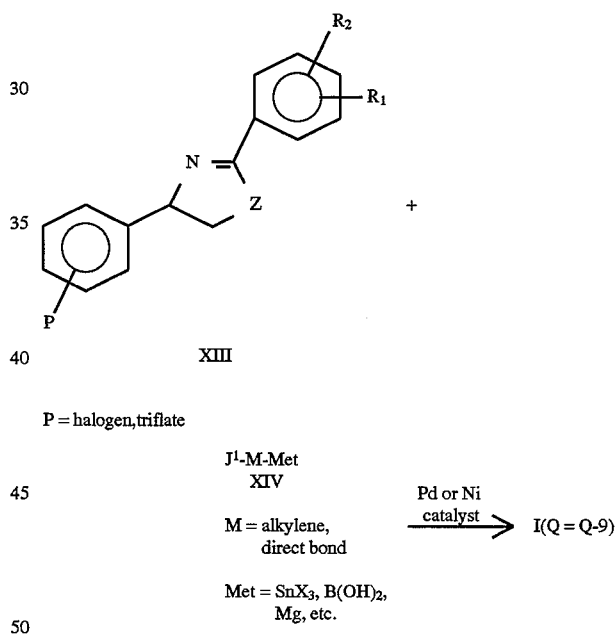

As shown in Scheme 10, compounds of Formula I where Q is phenyl and M is either O, S, or O-alkylene can be made by alkylation chemistry. Compounds of Formula XV where Q is phenyl substituted or OH or SH can be treated with a heterocycle of Formula XVI containing a leaving group (halogen, sulfonate, or sulfone for example) in the presence of an acid acceptor. The transformation is best carried out in an aprotic dipolar solvent such as dimethylformamide or dimethylacetamide. Depending on the reactivity of the heterocycle and the nature of the leaving group, a variety of acid acceptors and temperatures can be utilized. Some suitable bases am potassium carbonate, potassium-t-butoxide, and sodium hydride.

Scheme 10

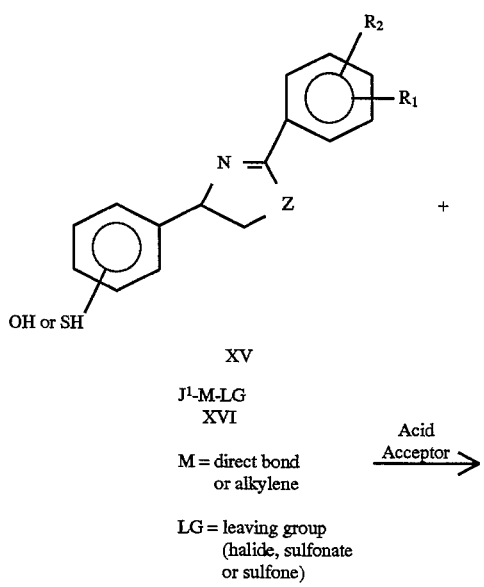

M = direct bond or alkylene

LG = leaving group (halide, sulfonate or sulfone)

$\xrightarrow{\text{Acid Acceptor}}$ I(Q = Q-9)

Compounds of Formula IV are known in the art. Heterocyclic compounds of Formula IV where Q=Q-1, Q-5, Q-6, and Q-8 are known and methods for the preparation of these compounds as well as compounds of Formula XIV and XVI can be found in Katritsky and Rees eds., "Comprehensive Heterocyclic Chemistry" Vol. 2–6, Pergamon Press, New York, (1984) and in Coffey ed., "Rodd's Chemistry of Carbon Compounds" Vol. IVa-1, Elsevier, Amsterdam, (1973–1980).

Compounds of Formula IV where Q=Q-2, Q-3, and Q-4 are also known. Methods for synthesis of these compounds can be found in European Patent Application 350,846; Berlin el. al., *J. Med. Chem.*, (1985) 28, 116–124; Dawson et al., *J. Med. Chem.*, (1984), 27, 1516–1531; and Olah, loc. cit., Vol. 2, 785–952. Compounds of Formula IV where Q=Q-7 are known and a review of the chemistry and synthesis of naphthalenes can be found in Coffey, loc. cit., Vol. IIIg, 99–284. These references also include functional group manipulations of the various Q groups which one skilled in the art can use to convert compounds of the instant invention to other compounds of the instant invention.

It is recognized that in many of the transformations described, it is necessary to utilize appropriate protecting groups to prevent unwanted side reactions or use reagents that do not affect functional groups other than those desired to be changed. One skilled in the art will be able to select appropriate protecting groups and reagents to this end.

EXAMPLE 1

2-(2,6-difluorophenyl)-4,5-dihydro-4-(2-naphthalenyl)-oxazole

Ethyl 2-naphthylacetate (11.6 g) was dissolved in ethanol (100 mL) and treated with solid sodium ethoxide (3.5 g) and then dropwise with n-butyl nitrite (7.6 mL). The reaction was stirred at 23° C. for 18 h and treated with acetic acid (5 mL) and stirred for 1 h. The ethanol was removed under reduced pressure and the residue was partitioned between ethyl acetate and water. The organic phase was dried over magnesium sulfate and evaporated under reduced pressure. The residue was chromatographed on silica gel with hexanes/ethyl acetate (5:1 to 3:1) as eluent. The crude residue (5.6 g) was taken up in ether (300 mL) cooled to 0° C. and treated with lithium aluminum hydride solution (45 mL, 1M in tetrahydrofuran) dropwise. The mixture was heated to reflux for 5 h and cooled. It was quenched by the sequential addition of ethyl acetate (5 mL) water (1.5 mL), sodium hydroxide solution (3M, 1.5 mL) and water (4 mL). The solid was filtered and the solution was dried with magnesium sulfate. The solvent was removed at reduced pressure and the solid was triturated with hexanes/butyl chloride (1:1, 100 mL). Of the crude 2-naphthylglycinol (2.6 g) thus obtained, 1.2 g was dissolved in tetrahydrofuran and treated with triethylamine (1 mL) and cooled in an ice water bath. Treatment of the mixture with 2,6-difluorobenzoyl chloride (1 mL) was followed by stirring at room temperature for 1 h. The mixture was diluted with dichloromethane and water. The organic phase was washed sequentially with sodium bicarbonate solution (saturated aqueous) and 1N hydrochloric acid. The solvent was dried with magnesium sulfate and removed under reduced pressure. The residue was chromatographed on silica gel with hexanes/ethyl acetate (5:1 to 1:1) as eluent. The product was treated with benzene (20 mL), thionyl chloride (3 mL) was added and the mixture heated at reflux for 2.5 h. The solvent was removed under reduced pressure and the residue was treated with methanol (20 mL) and NaOH (50% aqueous, 1.5 mL), and heated at reflux for 1 h. The mixture was evaporated under reduced pressure and the residue was partitioned between water and ethyl acetate. The ethyl acetate layer was dried over magnesium sulfate and evaporated under reduced pressure. The residue was chromatographed on silica gel using hexanes/ethyl acetate (5:1) as eluent to afford the title compound (0.68 g) as an oil which quickly solidified: mp 68°–70° C., $^{1}$H NMR (CDCl$_3$): 15 8.0–7.0 (m,10H, aryl H), 5.6 (m, 1H,CH), 4.9 (m, 1H,CH), 4.4 (m, 1H,CH).

EXAMPLE 2

Step A: [(2,6-difluorobenzoyl)amino]hydroxyacetic acid

A mixture of 50 g (0.318 mol) of 2,6-difluorobenzamide, 32 g (0.349 mol) of glyoxylic acid monohydrate and 200 mL of acetone was refluxed for 5 h. The reaction was cooled and solvents evaporated to give a white solid. It was triturated with cold acetone to afford 38.56 g of a white solid: mp 125°–127° C. $^{1}$H-NMR (DMSO-d$_6$)δ9.55 (d, 1H), 7.50 (m, 1H), 7.15 (t,2H), 5.45 (d,1H)

Step B: 5-bromo-α-[(2,6-difluorobenzoyl)amino]2-thiopheneacetic acid

A solution of 4.76 g (20.6 mmol) of the product of Step A in 140 mL of methanesulfonic acid was immersed in an ice-water bath (temperature between 5°–10° C.). Then, 4.0 g (24.6 mmol) of 2-bromothiophene was added dropwise. It was stirred at the same temperature until a deep blue-black color formed. It was poured into ice-water and the resulting precipitate was filtered. The solid was triturated with methylene chloride to give 4.05 g of a tan solid: mp 198°–199° C. (dec.). $^{1}$H-NMR (DMSO-d6) δ9.80 (d,1H), 7.55 (m, 1H), 7.20 (m,3H), 7.00 (d, 1H), 5.80 (d, 1H).

Step C: Methyl 5-bromo-α-[(2,6-difluorobenzoyl)amino]2-thiopheneacetate

An amount of 3.415 g (9 mmol) of the product of Step B was dissolved in 19 mL of methanol. It was cooled in an ice-bath and 1.13 mL of thionyl chloride was added dropwise. The mixture was heated at reflux for 30 min. It was cooled and the methanol removed under reduced pressure. A saturated solution of sodium bicarbonate was carefully added to the residue, then extracted with ether. The combined ether extracts were washed with brine, dried (MgSO$_4$) and concentrated to give a white solid: mp 123°–124° C.

¹H-NMR (DMSO-d6) δ9.90 (d, 1H), 7.55 (m, 1H), 7.20 (m,3H), 7.00 (d, 1H), 5.90 (d, 1H), 3.75 (s,3H).

Step D: 4-(5-bromo-2-thienyl)-2-(2,6-difluorophenyl)4,5-dihydrooxazole

An amount of 830 g (7.5 mmol) of anhydrous calcium chloride, 565 mg (15 mmol) of sodium borohydride and 15 mL of dry THF was stirred for 1 h. To this mixture was added 1.96 g (5 mmol) of the product of Step C in 10 mL of dry THF all at once. The resulting mixture was stirred at room temperature for 2 h. The reaction was immersed in an ice-bath and carefully quenched with 5% HCl and extracted with ethyl acetate. The combined ethyl acetate extracts were washed with brine, dried (MgSO₄) and concentrated to give 270 mg of a white solid. To a mixture of the solid, 111 mg( 1.1 mmol) of triethylamine, 0.68 mL of carbon tetrachloride and 3.5 mL of acetonitrile was added 289 mg( 1.1 mmol) of triphenylphosphine. The mixture was stirred at room temperature for 35 min. Solids were filtered and the residue washed several times with carbon tetrachloride. The combined filtrate and washings were concentrated. The residue was purified by passing through a silica gel flash column eluting with ethyl acetate: hexanes (1:2) to give an oil. ¹H-NMR (DMSO-d6) δ7.70 (m, 1H), 7.30 (t,2H), 7.15 (d, 1H), 6.95 (d, 1H), 5.70 (dd, 1H), 4.80 (t, 1H), 4.35 (t, 1H).

EXAMPLE 3

2-(2,6-difluorophenyl)-4,5-dihydro-4-(5-phenyl-2-thienyl)oxazole

To a solution of 100 mg (0.3 mmol) of the product of Step D of Example 2 in 0.6 mL toluene was added successively 10.4 mg (0.009 mmol) of Pd (PPh₃)₄, 0.3 mL of 2.0 m sodium carbonate, and 44 mg (0.36 mmol) of phenylboronic acid in 0.15 mL of methanol. The mixture was stirred at 80° C. for 2 h. It was cooled and partitioned between 25 mL of 2.0 m sodium carbonate containing 2.5 mL of ammonium hydroxide solution and 25 mL of methylene chloride. The methylene chloride layer was washed with brine, dried (MgSO₄), and concentrated. The residue was passed through a silica gel flash column eluting with ethyl acetate: hexanes (1:4) to give 85 mg of an oil. ¹H-NMR (CDCl₃) δ6.90–7.20 (m, 10H), 5.70 (dd,1H), 4.80 (t, 1H), 4.45 (t, 1H).

By the procedures described herein the following compounds of the Tables 1 to 20 can be prepared. The compounds in Table 1, line 1 can be referred to as 1-1, 1-2, 1-3 and 1-4 (as designated by line and column, respectively). All the other specific compounds covered in these Tables can be designated in an analogous fashion. In Tables 2–7, 9, 31–33, m is 1 when R⁶ is a single substituent and m is 2 when R⁶ is two substituents, which can be the same or different, as indicated in the table. The following abbreviations have been used in Tables 1–20: i=iso, n=normal, Me=methyl, Et=ethyl, Pr=propyl, Bu=butyl, Pen=pentyl, Hex=hexyl, Oct=octyl, Dec=decyl, Ph=phenyl, Pyr=pyridinyl.

Structures for Tables

T =

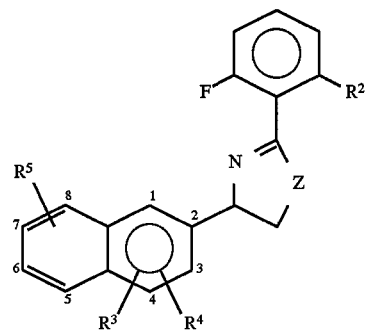

T-1

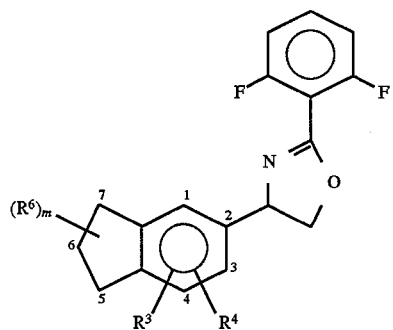

T-2

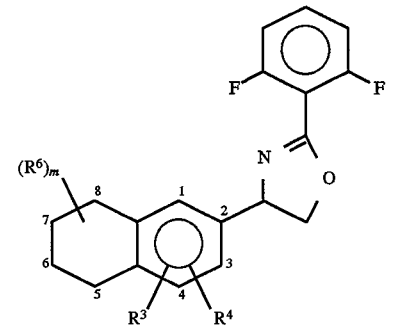

T-3

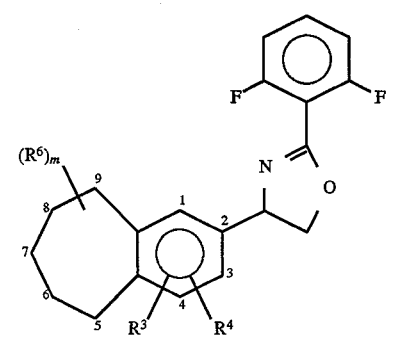

T-4

-continued
Structures for Tables
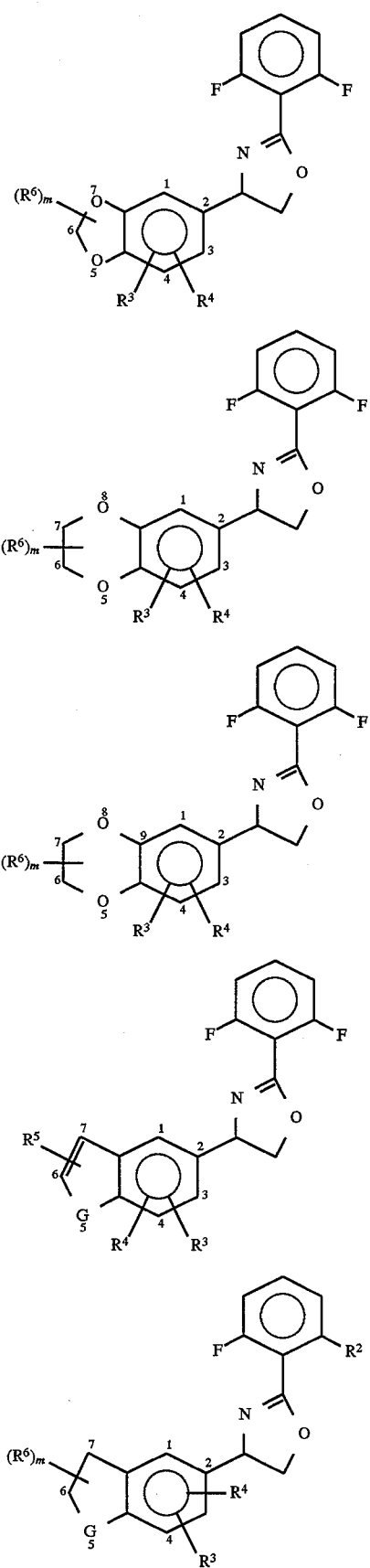
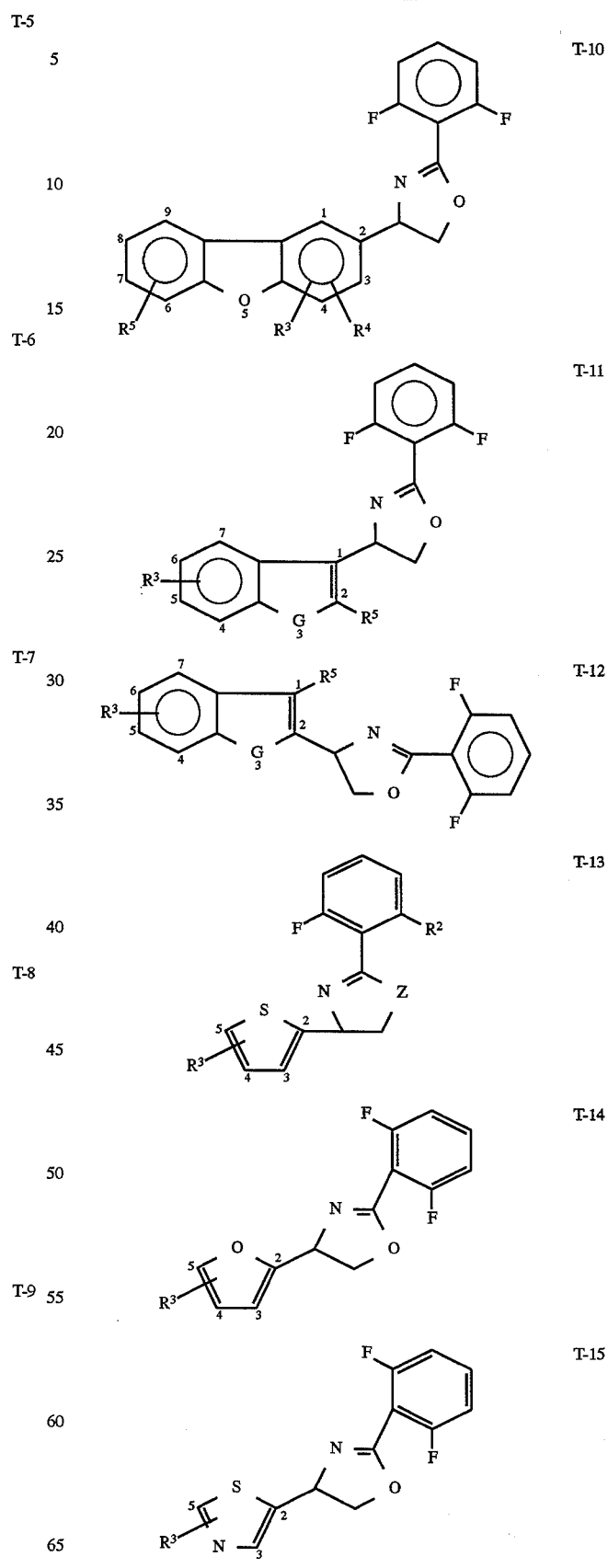

-continued
Structures for Tables
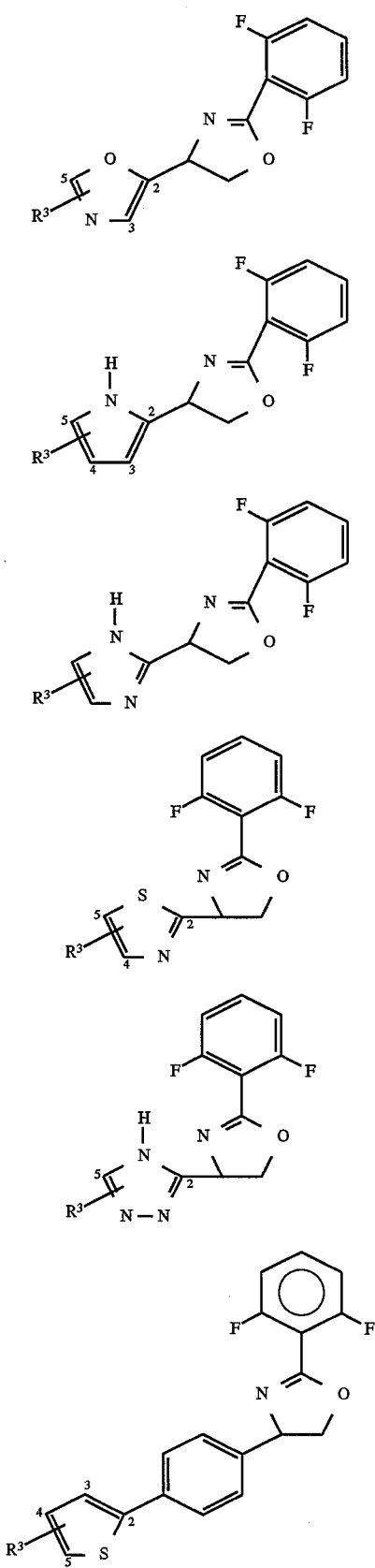
T-16
T-17
T-18
T-19
T-20
T-21
-continued
Structures for Tables
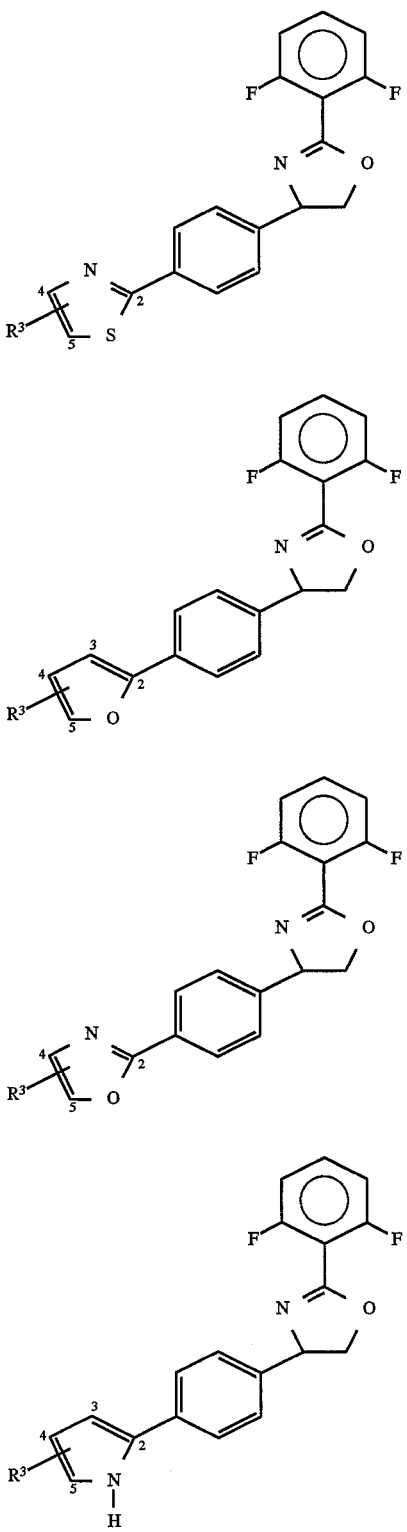
T-22
T-23
T-24
T-25

-continued
Structures for Tables
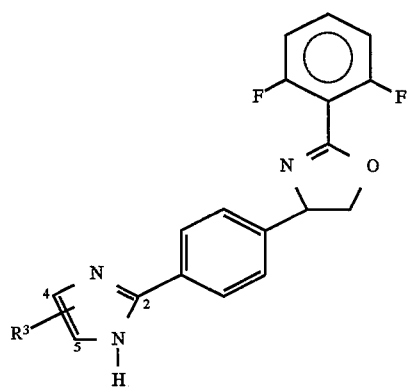
T-26
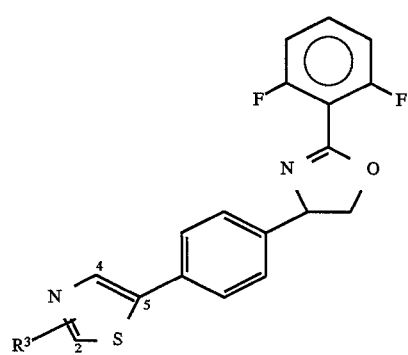
T-27
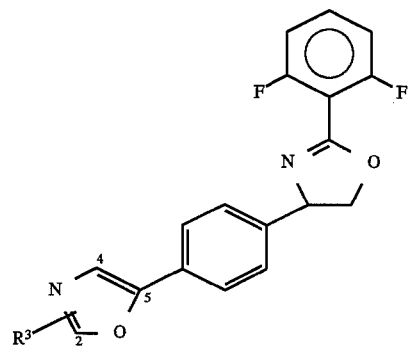
T-28
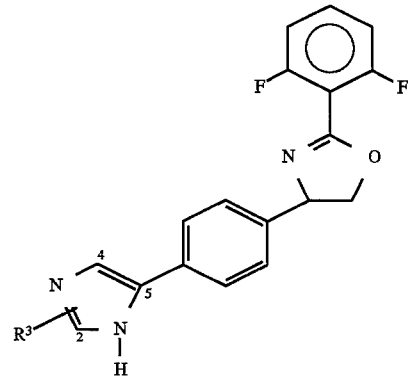
T-29
-continued
Structures for Tables
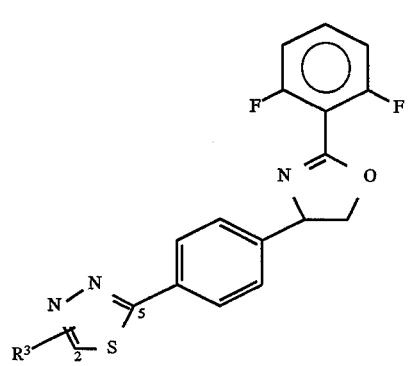
T-30
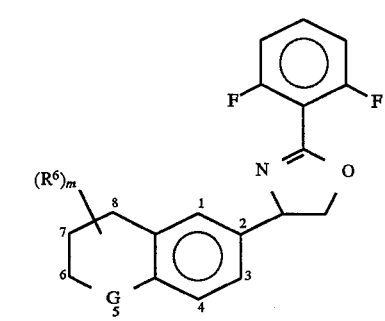
T-31
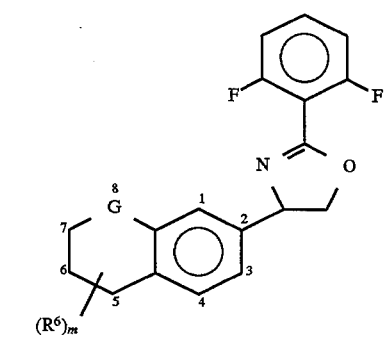
T-32
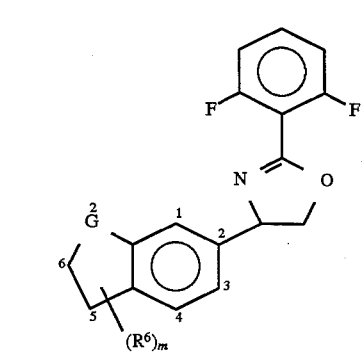
T-33

TABLE 1

| | 1 | 2 | 3 | 4 |
|---|---|---|---|---|
| | \multicolumn{4}{l}{$T = T\text{-}1, R^3 = R^4 = H, Z = O, R^2 = F, R^5 =$} |

| | 1 | 2 | 3 | 4 |
|---|---|---|---|---|
| 1 | 6-$CF_3$ | 5-$CH_2CH_3$ | 6-$OCH(CH_2)_2$ | 6-$CO(CH_2)_4CH_3$ |
| 2 | 6-Cl | 7-$(CH_2)_2CH_3$ | 7-$OCH(CH_2)_2$ | 6-COPh |
| 3 | 6-Br | 5-$(CH_2)_2CH_3$ | 6-$O(CH_2)_2CH_3$ | 6-CO(4-ClPh) |
| 4 | 5-$CF_3$ | 7-$(CH_2)_3CH_3$ | 7-$O(CH_2)_2CH_3$ | 6-CO(4-FPh) |
| 5 | 5-Cl | 5-$(CH_2)_3CH_3$ | 6-$O(CH_2)_3CH_3$ | 6-$CO_2CH_3$ |
| 6 | 5-Br | 7-$(CH_2)_4CH_3$ | 7-$O(CH_2)_3CH_3$ | 6-$CO_2CH_2CH_3$ |
| 7 | 7-$CF_3$ | 7-$(CH_2)_6CH_3$ | 6-$O(CH_2)_4CH_3$ | 6-$CO_2(CH_2)_2CH_3$ |
| 8 | 7-Cl | 7-$(CH_2)_8CH_3$ | 7-$O(CH_2)_4CH_3$ | 6-$CO_2CH(CH_2)_3$ |
| 9 | 7-Br | 7-$(CH_2)_{10}CH_3$ | 6-$O(CH_2)_5CH_3$ | 6-$CO_2C(CH_3)_3$ |
| 10 | 8-$CF_3$ | 7-$(CH_2)_{12}CH_3$ | 7-$O(CH_2)_5CH_3$ | 6-$CO_2(CH_2)_4CH_3$ |
| 11 | 8-Cl | 7-$(CH_2)_{14}CH_3$ | 6-$O(CH_2)_6CH$ | 6-$CO_2CH_2Ph$ |
| 12 | 8-Br | 6-$CH(CH_3)_2$ | 7-$O(CH_2)_6CH_3$ | 6-$CO_2Ph$ |
| 13 | 6-$CH_3$ | 7-$CH(CH_3)_2$ | 6-$O(CH_2)_7CH_3$ | 6-4-$CF_3Ph$ |
| 14 | 6-$CH_2CH_3$ | 5-$C(CH_3)_3$ | 6-$O(CH_2)_8CH_3$ | 6-$OCH_2OCH_2CH_3$ |
| 15 | 6-$(CH_2)_2CH_3$ | 6-$C(CH_3)_3$ | 6-$O(CH_2)_9CH_3$ | 6-$OCH_2$(4-ClPh) |
| 16 | 6-$(CH_2)_3CH_3$ | 7-$C(CH_3)_3$ | 6-$O(CH_2)_{10}CH_3$ | 6-$OCH_2$(3-ClPh) |
| 17 | 6-$(CH_2)_4CH_3$ | 8-$C(CH_3)_3$ | 6-$O(CH_2)_{12}CH_3$ | 6-$OCH_2$(2-ClPh) |
| 18 | 6-$(CH_2)_5CH_3$ | 6-$CH_2Ph$ | 6-$O(CH_2)_{14}CH_3$ | 6-$OCH_2$(4-MePh) |
| 19 | 6-$(CH_2)_6CH_3$ | 7-$CH_2Ph$ | 6-OPh | 6-$OCH_2$(3-MePh) |
| 20 | 6-$(CH_2)_7CH_3$ | 6-Ph | 7-OPh | 6-$OCH_2$(2-MePh) |
| 21 | 6-$(CH_2)_8CH_3$ | 7-Ph | 6-O-(2-Pyr) | 6-$OCH_2CH=CHCH_3$ |
| 22 | 6-$(CH_2)_9CH_3$ | 6-cyclohexyl | 6-$OCH_2Ph$ | 6-$OCH_2C(Cl)=CH_2$ |
| 23 | 6-$(CH_2)_{10}CH_3$ | 7-cyclohexyl | 6-$OCH_2$-4-ClPh | 6-$OCH_2C(CH_3)=CH_2$ |
| 24 | 6-$(CH_2)_{12}CH_3$ | 6-$OCH_3$ | 6-$OCH_2CH=CH_2$ | 6-(4-Cl-Ph) |
| 25 | 6-$(CH_2)_{14}CH_3$ | 7-$OCH_3$ | 6-$OCH_2C\equiv CH$ | 6-(3-Cl-Ph) |
| 26 | 7-$CH_3$ | 6-$OCH_2CH_3$ | 6-$OCH_2CH_2Ph$ | 6-(2-Cl-Ph) |
| 27 | 8-$CH_3$ | 7-$OCH_2CH_3$ | 6-$OCH_2OCH_3$ | 6-$OCHF_2$ |
| 28 | 5-$CH_3$ | 6-$OCH_2CF_3$ | 6-$COCH_3$ | 7-$OCHF_2$ |
| 29 | 7-$CH_2CH_3$ | 7-$OCH_2CF_3$ | 6-$COCH_2CH_3$ | 6-$OCH(CH_3)CH_2CH_3$ |
| 30 | 8-$CH_2CH_3$ | 6-$OCF_2CF_2H$ | 6-$CO(CH_2)_2CH_3$ | 6-O-cyclohexyl |
| | \multicolumn{4}{l}{$T = T\text{-}1, R^3 = R^4 = H, Z = O, R^2 = Cl, R^5$} |
| 31 | 6-$CF_3$ | 5-$CH_2CH_3$ | 6-$OCH(CH_2)_2$ | 6-$CO(CH_2)_4CH_3$ |
| 32 | 6-Cl | 7-$(CH_2)_2CH_3$ | 7-$OCH(CH_2)_2$ | 6-COPh |
| 33 | 6-Br | 5-$(CH_2)_2CH_3$ | 6-$O(CH_2)_2CH_3$ | 6-CO(4-ClPh) |
| 34 | 5-$CF_3$ | 7-$(CH_2)_3CH_3$ | 7-$O(CH_2)_2CH_3$ | 6-CO(4-FPh) |
| 35 | 5-Cl | 5-$(CH_2)_3CH_3$ | 6-$O(CH_2)_3CH_3$ | 6-$CO_2CH_3$ |
| 36 | 5-Br | 7-$(CH_2)_4CH_3$ | 7-$O(CH_2)_3CH_3$ | 6-$CO_2CH_2CH_3$ |
| 37 | 7-$CF_3$ | 7-$(CH_2)_6CH_3$ | 6-$O(CH_2)_4CH_3$ | 6-$CO_2(CH_2)_2CH_3$ |
| 38 | 7-Cl | 7-$(CH_2)_8CH_3$ | 7-$O(CH_2)_4CH_3$ | 6-$CO_2CH(CH_2)_3$ |
| 39 | 7-Br | 7-$(CH_2)_{10}CH_3$ | 6-$O(CH_2)_5CH_3$ | 6-$CO_2C(CH_3)_3$ |
| 40 | 8-$CF_3$ | 7-$(CH_2)_{12}CH_3$ | 7-$O(CH_2)_5CH_3$ | 6-$CO_2(CH_2)_4CH_3$ |
| 41 | 8-Cl | 7-$(CH_2)_{14}CH_3$ | 6-$O(CH_2)_6CH_3$ | 6-$CO_2CH_2Ph$ |
| 42 | 8-Br | 6-$CH(CH_3)_2$ | 7-$O(CH_2)_6CH_3$ | 6-$CO_2Ph$ |
| 43 | 6-$CH_3$ | 7-$CH(CH_3)_2$ | 6-$O(CH_2)_7CH_3$ | 6-4-$CF_3$-Ph |
| 44 | 6-$CH_2CH_3$ | 5-$C(CH_3)_3$ | 6-$O(CH_2)_8CH_3$ | 6-$OCH_2OCH_2CH_3$ |
| 45 | 6-$(CH_2)_2CH_3$ | 6-$C(CH_3)_3$ | 6-$O(CH_2)_9CH_3$ | 6-$OCH_2$(4-ClPh) |
| 46 | 6-$(CH_2)_3CH_3$ | 7-$C(CH_3)_3$ | 6-$O(CH_2)_{10}CH_3$ | 6-$OCH_2$(3-ClPh) |
| 47 | 6-$(CH_2)_4CH_3$ | 8-$C(CH_3)_3$ | 6-$O(CH_2)_{12}CH_3$ | 6-$OCH_2$(2-ClPh) |
| 48 | 6-$(CH_2)_5CH_3$ | 6-$CH_2Ph$ | 6-$O(CH_2)_{14}CH_3$ | 6-$OCH_2$(4-MePh) |
| 49 | 6-$(CH_2)_6CH_3$ | 7-$CH_2Ph$ | 6-OPh | 6-$OCH_2$(3-MePh) |
| 50 | 6-$(CH_2)_7CH_3$ | 6-Ph | 7-OPh | 6-$OCH_2$(2-MePh) |
| 51 | 6-$(CH_2)_8CH_3$ | 7-Ph | 6-O-(2-Pyr) | 6-$OCH_2CH=CHCH_3$ |
| 52 | 6-$(CH_2)_9CH_3$ | 6-cyclohexyl | 6-$OCH_2Ph$ | 6-$OCH_2C(Cl)=CH_2$ |
| 53 | 6-$(CH_2)_{10}CH_3$ | 7-cyclohexyl | 6-$OCH_2$-4-ClPh | 6-$OCH_2C(CH_3)=CH_2$ |
| 54 | 6-$(CH_2)_{12}CH_3$ | 6-$OCH_3$ | 6-$OCH_2CH=CH_2$ | 6-(4-Cl-Ph) |
| 55 | 6-$(CH_2)_{14}CH_3$ | 7-$OCH_3$ | 6-$OCH_2C\equiv CH$ | 6-(3-Cl-Ph) |
| 56 | 7-$CH_3$ | 6-$OCH_2CH_3$ | 6-$OCH_2CH_2Ph$ | 6-(2-Cl-Ph) |
| 57 | 8-$CH_3$ | 7-$OCH_2CH_3$ | 6-$OCH_2OCH_3$ | 6-$OCHF_2$ |
| 58 | 5-$CH_3$ | 6-$OCH_2CF_3$ | 6-$COCH_3$ | 7-$OCHF_2$ |
| 59 | 7-$CH_2CH_3$ | 7-$OCH_2CF_3$ | 6-$COCH_2CH_3$ | 6-$OCH(CH_3)CH_2CH_3$ |
| 60 | 8-$CH_2CH_3$ | 6-$OCF_2CF_2H$ | 6-$CO(CH_2)_2CH_3$ | 6-O-cyclohexyl |
| | \multicolumn{4}{l}{$T = T\text{-}1, R^3 = 3\text{-}Cl, R^4 = H, Z = O, R^2 = F, R^5 =$} |
| 61 | 6-H | 5-$CF_3$ | 6-$CF_3$ | 7-$CF_3$ |
| 62 | 5-Cl | 6-Cl | 7-Cl | 5-$CH_3$ |
| 63 | 6-$CH_3$ | 7-$CH_3$ | 5-$C(CH_3)_3$ | 6-$C(CH_3)_3$ |
| 64 | 7-$C(CH_3)_3$ | 6-$(CH_2)_2CH_3$ | 6-$(CH_2)_3CH_3$ | 6-$(CH_2)_4CH_3$ |
| 65 | 6-$(CH_2)_6CH_3$ | 6-$(CH_2)_8CH_3$ | 6-$OCH_3$ | 6-$OCH_2CH_3$ |
| 66 | 6-$OCH(CH_3)_2$ | 6-$O(CH_2)_2CH_3$ | 6-$O(CH_2)_3CH_3$ | 6-$O(CH_2)_4CH_3$ |
| 67 | 6-$O(CH_2)_6CH_3$ | 6-$O(CH_2)_8CH_3$ | 6-$OCF_2CF_2H$ | 6-$OCH_2CF_3$ |
| 68 | 6-$OCH_2OCH_3$ | 6-OPh | 6-$OCH_2Ph$ | 6-$CO_2CH_3$ |
| 69 | 6-$COCH_3$ | 6-Ph | 7-Ph | 7-OPh |
| 70 | 6-COPh | 6-$COCF_3$ | 6-$O(CH_2)_2Ph$ | 6-$CH_2Ph$ |

TABLE 1-continued

T = T-1, R³ = R⁴ = H, Z = S, R² = F, R⁵ =

| | 1 | 2 | 3 | 4 |
|---|---|---|---|---|
| 71 | 6-H | 5-CF₃ | 6-CF₃ | 7-CF₃ |
| 72 | 5-Cl | 6-Cl | 7-Cl | 5-CH₃ |
| 73 | 6-CH₃ | 7-CH₃ | 5-C(CH₃)₃ | 6-C(CH₃)₃ |
| 74 | 7-C(CH₃)₃ | 6-(CH₂)₂CH₃ | 6-(CH₂)₃CH₃ | 6-(CH₂)₄CH₃ |
| 75 | 6-(CH₂)₆CH₃ | 6-(CH₂)₈CH₃ | 6-OCH₃ | 6-OCH₂CH₃ |
| 76 | 6-OCH(CH₃)₂ | 6-O(CH₂)₂CH₃ | 6-O(CH₂)₃CH₃ | 6-O(CH₂)₄CH₃ |
| 77 | 6-O(CH₂)₆CH₃ | 6-O(CH₂)₈CH₃ | 6-OCF₂CF₂H | 6-OCH₂CF₃ |
| 78 | 6-OCH₂OCH₃ | 6-OPh | 6-OCH₂Ph | 6-CO₂CH₃ |
| 79 | 6-COCH₃ | 6-Ph | 7-Ph | 7-OPh |
| 80 | 6-COPh | 6-COCF₃ | 6-O(CH₂)₂Ph | 6-CH₂Ph |

TABLE 2

T = T-2, R³ = R⁴ = H, m = 1 or 2, R⁶ =

| | 1 | 2 | 3 | 4 |
|---|---|---|---|---|
| 81 | H | 5-Me | 5-Et | 5-n-Pr |
| 82 | 5-n-Bu | 5-n-Hex | 6-Me | 6-Et |
| 83 | 6-n-Bu | 7-Me | 7-Et | 5,5-diMe |
| 84 | 5,5-diEt | 5-Me,5-Et | 6,6-diMe | 6,6-diEt |
| 85 | 7,7-diMe | 5-Me,6-Me | 5-Me,6-Me | 5-Me,7-Me |

TABLE 3

T = T-3, R³ = R⁴ = H, m = 1 or 2, R⁶ =

| | 1 | 2 | 3 | 4 |
|---|---|---|---|---|
| 86 | H | 5-Me | 5-Et | 5-n-Pr |
| 87 | 5-n-Bu | 6-Me | 7-Me | 8-Me |
| 88 | 5,5-diMe | 6,6-diMe | 7,7-diMe | 8,8-diMe |
| 89 | 6-Et | 6-n-Bu | 7-Et | 7-n-Bu |
| 90 | 8-Et | 8-n-Bu | 5-n-Hex | 6-n-Hex |

TABLE 4

T = T-4, R³ = R⁴ = H, m = 1 or 2, R⁶ =

| | 1 | 2 | 3 | 4 |
|---|---|---|---|---|
| 91 | H | 5-Me | 5-Et | 5-n-Pr |
| 92 | 6-Me | 7-Me | 8-Me | 9-Me |
| 93 | 6,6-diMe | 7,7-diMe | 8,8-diMe | 9,9-diMe |
| 94 | 6-Et | 7-Et | 8-Et | 9-Et |
| 95 | 5-n-Bu | 5-n-Hex | 9-n-Bu | 9-n-Hex |

TABLE 5

T = T-5, R³ = R⁴ = H, m = 1 or 2, R⁶ =

| | 1 | 2 | 3 | 4 |
|---|---|---|---|---|
| 96 | H | 6-Me | 6-Et | 6-n-Pr |
| 97 | 6-n-Bu | 6-n-Pen | 6-n-Oct | 6-n-Dec |
| 98 | 6-i-Pr | 6-t-Bu | 6,6-diF | 6,6-diMe |
| 99 | 6-Ph | 6-(3-Cl-Ph) | 6-(2-Cl-Ph) | 6-Me,6-Et |
| 100 | 6-Me,6-Ph | 6-Me,6-n-Bu | 6-Me,6-n-Hex | 6,6-diEt |

TABLE 6

T = T-6, R³ = R⁴ = H, m = 1 or 2, R⁶ =

| | 1 | 2 | 3 | 4 |
|---|---|---|---|---|
| 101 | H | 6-Me | 6-Et | 6-n-Pr |
| 102 | 7-Me | 7-Et | 7-n-Pr | 6,6-diMe |
| 103 | 6-n-Bu | 6-n-Hex | 6,6-diEt | 7,7-diMe |
| 104 | 7,7-diEt | 6-Ph | 7-Ph | 6-Me,6-Et |

TABLE 7

T = T-7, R³ = R⁴ = H, m = 1 or 2, R⁶ =

| | 1 | 2 | 3 | 4 |
|---|---|---|---|---|
| 105 | H | 6-Me | 7-Me | 8-Me |
| 106 | 6-Et | 7-Et | 8-Et | 6,6-diMe |
| 107 | 7,7-diMe | 6,6-diEt | 6-Ph | 7-Ph |
| 108 | 8-Ph | 6-Me,6-Et | 6-Me,6-Ph | 7-Me,7-Ph |

TABLE 8

| | 1 | 2 | 3 | 4 |
|---|---|---|---|---|

T = T-8, R³ = R⁴ = H, G = S, R⁵ =

| | 1 | 2 | 3 | 4 |
|---|---|---|---|---|
| 109 | H | 6-Bu | 7-Bu | 6-CF₃ |
| 110 | 7-CF₃ | 6-Me | 7-Me | 6-Et |
| 111 | 7-Et | 6-n-Pr | 6-i-Pr | 6-n-Bu |
| 112 | 6-n-Hex | 6-n-Oct | 6-OMe | 6-OEt |
| 113 | 6-O-n-Pr | 6-O-i-Pr | 6-O-n-Bu | 6-O-n-Hex |
| 114 | 6-O-n-Oct | 6-COCH₃ | 6-CO₂Et | 6-COPh |

T = T-8, R³ = R⁴ = H, G = S, R⁵ =

| | 1 | 2 | 3 | 4 |
|---|---|---|---|---|
| 115 | H | 6-Bu | 7-Bu | 6-CF₃ |
| 116 | 7-CF₃ | 6-Me | 7-Me | 6-Et |
| 117 | 7-Et | 6-n-Pr | 6-i-Pr | 6-n-Bu |
| 118 | 6-n-Hex | 6-n-Oct | 6-OMe | 6-OEt |
| 119 | 6-O-n-Pr | 6-O-i-Pr | 6-O-n-Bu | 6-O-n-Hex |
| 120 | 6-O-n-Oct | 6-COCH₃ | 6-CO₂Et | 6-COPh |

TABLE 9

| | 1 | 2 | 3 | 4 |
|---|---|---|---|---|

T = T-9, R³ = R⁴ = H, G = O, R² = F, m = 1 or 2, R⁶ =

| | 1 | 2 | 3 | 4 |
|---|---|---|---|---|
| 121 | 6-H | 6-Me | 6-Et | 6-n-Pr |
| 122 | 6-n-Bu | 6-n-Hex | 6-n-Oct | 6,6-diMe |
| 123 | 6,6-diEt | 6-Me,6-Et | 6-Me,6-Ph | 6-Me,6-n-Bu |
| 124 | 7-Me | 7-Et | 7-n-Pr | 7-n-Bu |

TABLE 9-continued

| | 1 | 2 | 3 | 4 |
|---|---|---|---|---|
| | T = T-9, $R^3$ = $R^4$ = H, G = O, $R^2$ = Cl, m = 1 or 2, $R^6$ = | | | |
| 125 | 6-H | 6-Me | 6-Et | 6-n-Pr |
| 126 | 6-n-Bu | 6-n-Hex | 6-n-Oct | 6,6-diMe |
| 127 | 6,6-diEt | 6-Me,6-Et | 6-Me,6-Ph | 6-Me,6-n-Bu |
| 128 | 7-Me | 7-Et | 7-n-Pr | 7-n-Bu |
| | T = T-9, $R^3$ = $R^4$ = H, G = S, $R^2$ = F, m = 1 or 2, $R^6$ = | | | |
| 129 | 6-H | 6-Me | 6-Et | 6-n-Pr |
| 130 | 6-n-Bu | 6-n-Hex | 6-n-Oct | 6,6-diMe |
| 131 | 6,6-diEt | 6-Me,6-Et | 6-Me,6-Ph | 6-Me,6-n-Bu |
| 132 | 7-Me | 7-Et | 7-n-Pr | 7-n-Bu |
| | T = T-9, $R^3$ = $R^4$ = H, G = S, $R^2$ = Cl, m = 1 or 2, $R^6$ = | | | |
| 133 | 6-H | 6-Me | 6-Et | 6-n-Pr |
| 134 | 6-n-Bu | 6-n-Hex | 6-n-Oct | 6,6-diMe |
| 135 | 6,6-diEt | 6-Me,6-Et | 6-Me,6-Ph | 6-Me,6-n-Bu |
| 136 | 7-Me | 7-Et | 7-n-Pr | 7-n-Bu |

TABLE 10

| | 1 | 2 | 3 | 4 |
|---|---|---|---|---|
| | T = T-10, $R^3$ = $R^4$ = H, $R^5$ = | | | |
| 137 | H | 7-Bu | 8-Bu | 7-Cl |
| 138 | 8-Cl | 6-Cl | 5-Cl | 7-CF$_3$ |
| 139 | 8-CF$_3$ | 8-Me | 7-Me | 8-Et |
| 140 | 7-Et | 8-n-Pr | 8-n-Bu | 8-n-Hex |
| 141 | 8-n-Oct | 8-i-Pr | 8-OMe | 8-OEt |
| 142 | 8-OCH$_2$CF$_3$ | 8-O-n-Bu | 8-CO$_2$Et | 8-COCH$_3$ |

TABLE 11

| | 1 | 2 | 3 | 4 |
|---|---|---|---|---|
| | T = T-11, $R^5$ = H, G = O, $R^3$ = | | | |
| 143 | H | 5-Cl | 6-Cl | 7-Cl |
| 144 | 4-Cl | 5-CF$_3$ | 6-CF$_3$ | 5-Me |
| 145 | 5-Et | 5-n-Pr | 5-n-Bu | 5-n-Hex |
| 146 | 5-n-Oct | 6-Me | 6-Et | 6-n-Bu |
| 147 | 5-OMe | 5-OEt | 5-O-i-Pr | 5-O-n-Pr |
| 148 | 5-O-n-Pr | 5-O-n-Hex | 5-O-n-Oct | 6-OMe |
| 149 | 6-OEt | 6-O-i-Pr | 5-CO$_2$Et | 5-COCH$_3$ |

TABLE 11-continued

| | 1 | 2 | 3 | 4 |
|---|---|---|---|---|
| 150 | 5-COPh | 6-CO$_2$Et | 6-COCH$_3$ | 6-COPh |
| | T = T-11, $R^5$ = H, G = S, $R^3$ = | | | |
| 151 | H | 5-Cl | 6-Cl | 7-Cl |
| 152 | 4-Cl | 5-CF$_3$ | 6-CF$_3$ | 5-Me |
| 153 | 5-Et | 5-n-Pr | 5-n-Bu | 5-n-Hex |
| 154 | 5-n-Oct | 6-Me | 6-Et | 6-n-Bu |
| 155 | 5-OMe | 5-OEt | 5-O-i-Pr | 5-O-n-Pr |
| 156 | 5-O-n-Pr | 5-O-n-Hex | 5-O-n-Oct | 6-OMe |
| 157 | 6-OEt | 6-O-i-Pr | 5-CO$_2$Et | 5-COCH$_3$ |
| 158 | 5-COPh | 6-CO$_2$Et | 6-COCH$_3$ | 6-COPh |

TABLE 12

| | 1 | 2 | 3 | 4 |
|---|---|---|---|---|
| | T = T-12, $R^5$ = H, G = O, $R^3$ = | | | |
| 159 | H | 5-Cl | 6-Cl | 7-Cl |
| 160 | 4-Cl | 5-CF$_3$ | 6-CF$_3$ | 5-Me |
| 161 | 5-Et | 5-n-Pr | 5-n-Bu | 5-n-Hex |
| 162 | 5-n-Oct | 6-Me | 6-Et | 6-n-Bu |
| 163 | 5-OMe | 5-OEt | 5-O-i-Pr | 5-O-n-Pr |
| 164 | 5-O-n-Pr | 5-O-n-Hex | 5-O-n-Oct | 6-OMe |
| 165 | 6-OEt | 6-O-i-Pr | 5-CO$_2$Et | 5-COCH$_3$ |
| 166 | 5-COPh | 6-CO$_2$Et | 6-COCH$_3$ | 6-COPh |
| | T = T-12, $R^5$ = H, G = S, $R^3$ = | | | |
| 167 | H | 5-Cl | 6-Cl | 7-Cl |
| 168 | 4-Cl | 5-CF$_3$ | 6-CF$_3$ | 5-Me |
| 169 | 5-Et | 5-n-Pr | 5-n-Bu | 5-n-Hex |
| 170 | 5-n-Oct | 6-Me | 6-Et | 6-n-Bu |
| 171 | 5-OMe | 5-OEt | 5-O-i-Pr | 5-O-n-Pr |
| 172 | 5-O-n-Pr | 5-O-n-Hex | 5-O-n-Oct | 6-OMe |
| 173 | 6-OEt | 6-O-i-Pr | 5-CO$_2$Et | 5-COCH$_3$ |
| 174 | 5-COPh | 6-CO$_2$Et | 6-COCH$_3$ | 6-COPh |

TABLE 13

| | 1 | 2 | 3 | 4 |
|---|---|---|---|---|
| | T = T-13, $R^2$ = F, Z = O, $R^3$ = | | | |
| 175 | 5-CF$_3$ | 5-C(CH$_3$)$_3$ | 5-CH$_2$(4-Cl-Ph) | 5-(4-Cl-Ph) |
| 176 | 4-CF$_3$ | 4-C(CH$_3$)$_3$ | 4-CH$_2$(4-Cl-Ph) | 4-(4-Cl-Ph) |
| 177 | 5-Cl | 5-CH(CH$_3$)$_2$ | 5-CH$_2$(4-Br-Ph) | 5-(4-Br-Ph) |
| 178 | 4-Cl | 4-CH(CH$_3$)$_2$ | 5-CH$_2$(4-CF$_3$-Ph) | 5-(4-CF$_3$-Ph) |
| 179 | 5-Br | 5-cyclohexyl | 4-CH$_2$(4-CF$_3$-Ph) | 4-(4-CF$_3$-Ph) |
| 180 | 4-Br | 4-cyclohexyl | 5-CH$_2$(3-Br-Ph) | 5-(3-Br-Ph) |
| 181 | 5-CH$_3$ | 5-O(CH$_2$)$_5$CH$_3$ | 5-CH$_2$(3-CF$_3$-Ph) | 5-(3-CF$_3$-Ph) |
| 182 | 4-CH$_3$ | 4-O(CH$_2$)$_5$CH$_3$ | 5-CH$_2$(2-Cl-Ph) | 5-(2-Cl-Ph) |
| 183 | 5-CH$_2$CH$_3$ | 5-O(CH$_2$)$_7$CH$_3$ | 5-CH$_2$(4-OMe-Ph) | 5-(4-OMe-Ph) |
| 184 | 4-CH$_2$CH$_3$ | 4-O(CH$_2$)$_7$CH$_3$ | 5-CH$_2$(2,4-di-Cl-Ph) | 5-(2,4-di-Cl-Ph) |
| 185 | 5-(CH$_2$)$_2$CH$_3$ | 5-O(CH$_2$)$_9$CH$_3$ | 4-CH$_2$(2,4-di-Cl-Ph) | 4-(2,4-di-Cl-Ph) |
| 186 | 4-(CH$_2$)$_2$CH$_3$ | 4-O(CH$_2$)$_9$CH$_3$ | 5-CH$_2$(2,5-di-Cl-Ph) | 5-(2,5-di-Cl-Ph) |
| 187 | 5-(CH$_2$)$_3$CH$_3$ | 5-O(CH$_2$)$_{11}$CH$_3$ | 5-CH$_2$(2,3-di-Cl-Ph) | 5-(2,3-di-Cl-Ph) |
| 188 | 4-(CH$_2$)$_3$CH$_3$ | 4-O(CH$_2$)$_{11}$CH$_3$ | 5-CH$_2$(2,6-di-Cl-Ph) | 5-(2,6-di-Cl-Ph) |
| 189 | 5-(CH$_2$)$_4$CH$_3$ | 5-OPh | 5-CH$_2$(3,4-di-Cl-Ph) | 5-(3,4-di-Cl-Ph) |
| 190 | 4-(CH$_2$)$_4$CH$_3$ | 4-OPh | 5-CH$_2$(3,5-di-Cl-Ph) | 5-(3,5-di-Cl-Ph) |

TABLE 13-continued

|  | 1 | 2 | 3 | 4 |
|---|---|---|---|---|
| 191 | 5-$(CH_2)_5CH_3$ | 5-$OCH_2Ph$ | 5-$CH_2$(3-Cl,4-F-Ph) | 5-(3-Cl,4-F-Ph) |
| 192 | 4-$(CH_2)_5CH_3$ | 5-$OCH_2Ph$ | 5-$CH_2$(2-Cl,4-$CF_3$-Ph) | 5-(2-Cl,4-$CF_3$-Ph) |
| 193 | 5-$(CH_2)_6CH_3$ | 5-Pyr | 4-$CH_2$(2-Cl,4-$CF_3$-Ph) | 4-(2-Cl,4-$CF_3$-Ph) |
| 194 | 4-$(CH_2)_6CH_3$ | 4-Pyr | 5-$CH_2$(2-F,5-OMe-Ph) | 5-(2-F,5-OMe-Ph) |

T = T-13, $R^2$ = F, Z = O, $R^3$ =

| 195 | 5-$(CH_2)_7CH_3$ | 5-$CH_2Pyr$ | 5-$CH_2$(2-F,5-Me-Ph) | 5-(2-F,5-Me-Ph) |
|---|---|---|---|---|
| 196 | 4-$(CH_2)_7CH_3$ | 4-$CH_2Pyr$ | 5-$CH_2$(2,4,5-tri-Cl-Ph) | 5-(2,4,5-tri-Cl-Ph) |
| 197 | 5-$(CH_2)_8CH_3$ | 5-O-Pyr | 4-$CH_2$(2,4,5-tri-Cl-Ph) | 4-(2,4,5-tri-Cl-Ph) |
| 198 | 4-$(CH_2)_8CH_3$ | 4-O-Pyr | 5-$CH_2$(2,4,5-tri-F-Ph) | 5-(2,4,5-tri-F-Ph) |
| 199 | 5-$(CH_2)_9CH_3$ | 5-$CH_2Ph$ | 5-$CH_2$(2,4-di-Cl,5-$CF_3$-Ph) | 5-(2,4-di-Cl,5-$CF_3$-Ph) |
| 200 | 4-$(CH_2)_9CH_3$ | 4-$CH_2Ph$ | 4-$CH_2$(2,4-di-Cl,5-$CF_3$-Ph) | 4-(2,4-di-Cl,5-$CF_3$-Ph) |
| 201 | 5-$(CH_2)_{11}CH_3$ | 5-Ph | 5-$CH_2$(2-Cl,5-$CO_2Me$-Ph) | 5-(2-Cl,5-$CO_2Me$-Ph) |
| 202 | 4-$(CH_2)_{11}CH_3$ | 4-Ph | 4-$CH_2$(2-Cl,5-$CO_2Me$-Ph) | 4-(2-Cl,5-$CO_2Me$-Ph) |
| 203 | 5-$(CH_2)_{13}CH_3$ | 5-O-cyclohexyl | 5-$CH_2$(2,4-di-Cl,5-OMe-Ph) | 5-(2,4-di-Cl,5-OMe-Ph) |
| 204 | 4-$(CH_2)_{13}CH_3$ | 4-O-cyclohexyl | 4-$CH_2$(2,4-di-Cl,5-OMe-Ph) | 4-(2,4-di-Cl,5-OMe-Ph) |

T = T-13, $R^2$ = Cl, Z = O, $R^3$ =

| 205 | 5-$CF_3$ | 5-$C(CH_3)_3$ | 5-$CH_2$(4-Cl-Ph) | 5-(4-Cl-Ph) |
|---|---|---|---|---|
| 206 | 4-$CF_3$ | 4-$C(CH_3)_3$ | 5-$CH_2$(4-Br-Ph) | 5-(4-Br-Ph) |
| 207 | 4-Cl | 4-$CH(CH_3)_2$ | 5-$CH_2$(4-$CF_3$-Ph) | 5-(4-$CF_3$-Ph) |
| 208 | 5-Br | 5-cyclohexyl | 4-$CH_2$(4-$CF_3$-Ph) | 4-(4-$CF_3$-Ph) |
| 209 | 4-Br | 4-cyclohexyl | 5-$CH_2$(3-Br-Ph) | 5-(3-Br-Ph) |
| 210 | 5-$CH_3$ | 5-$O(CH_2)_5CH_3$ | 5-$CH_2$(3-$CF_3$-Ph) | 5-(3-$CF_3$-Ph) |
| 211 | 4-$CH_3$ | 4-$O(CH_2)_5CH_3$ | 5-$CH_2$(2-Cl-Ph) | 5-(2-Cl-Ph) |
| 212 | 5-$CH_2CH_3$ | 5-$O(CH_2)_7CH_3$ | 5-$CH_2$(4-OMe-Ph) | 5-(4-OMe-Ph) |
| 213 | 4-$CH_2CH_3$ | 4-$O(CH_2)_7CH_3$ | 5-$CH_2$(2,4-di-Cl-Ph) | 5-(2,4-di-Cl-Ph) |
| 214 | 5-$(CH_2)_2CH_3$ | 5-$O(CH_2)_9CH_3$ | 4-$CH_2$(2,4-di-Cl-Ph) | 4-(2,4-di-Cl-Ph) |
| 215 | 4-$(CH_2)_2CH_3$ | 4-$O(CH_2)_9CH_3$ | 5-$CH_2$(2,5-di-Cl-Ph) | 5-(2,5-di-Cl-Ph) |
| 216 | 5-$(CH_2)_3CH_3$ | 5-$O(CH_2)_{11}CH_3$ | 5-$CH_2$(2,3-di-Cl-Ph) | 5-(2,3-di-Cl-Ph) |
| 217 | 4-$(CH_2)_3CH_3$ | 4-$O(CH_2)_{11}CH_3$ | 5-$CH_2$(2,6-di-Cl-Ph) | 5-(2,6-di-Cl-Ph) |
| 218 | 5-$(CH_2)_4CH_3$ | 5-OPh | 5-$CH_2$(3,4-di-Cl-Ph) | 5-(3,4-di-Cl-Ph) |
| 219 | 4-$(CH_2)_4CH_3$ | 4-OPh | 5-$CH_2$(3,5-di-Cl-Ph) | 5-(3,5-di-Cl-Ph) |
| 220 | 5-$(CH_2)_5CH_3$ | 5-$OCH_2Ph$ | 5-$CH_2$(3-Cl,4-F-Ph) | 5-(3-Cl,4-F-Ph) |

T = T-13, $R^2$ = Cl, Z = O, $R^3$ =

| 221 | 4-$(CH_2)_5CH_3$ | 5-$OCH_2Ph$ | 5-$CH_2$(2-Cl,4-$CF_3$-Ph) | 5-(2-Cl,4-$CF_3$-Ph) |
|---|---|---|---|---|
| 222 | 5-$(CH_2)_6CH_3$ | 5-Pyr | 4-$CH_2$(2-Cl,4-$CF_3$-Ph) | 4-(2-Cl,4-$CF_3$-Ph) |
| 223 | 4-$(CH_2)_6CH_3$ | 4-Pyr | 5-$CH_2$(2-F,5-OMe-Ph) | 5-(2-F,5-OMe-Ph) |
| 224 | 5-$(CH_2)_7CH_3$ | 5-$CH_2Pyr$ | 5-$CH_2$(2-F,5-Me-Ph) | 5-(2-F,5-Me-Ph) |
| 225 | 4-$(CH_2)_7CH_3$ | 4-$CH_2Pyr$ | 5-$CH_2$(2,4,5-tri-Cl-Ph) | 5-(2,4,5-tri-Cl-Ph) |
| 226 | 5-$(CH_2)_8CH_3$ | 5-O-Pyr | 4-$CH_2$(2,4,5-tri-Cl-Ph) | 4-(2,4,5-tri-Cl-Ph) |
| 227 | 4-$(CH_2)_8CH_3$ | 4-O-Pyr | 5-$CH_2$(2,4,5-tri-F-Ph) | 5-(2,4,5-tri-F-Ph) |
| 228 | 5-$(CH_2)_9CH_3$ | 5-$CH_2Ph$ | 5-$CH_2$(2,4-di-Cl,5-$CF_3$-Ph) | 5-(2,4-di-Cl,5-$CF_3$-Ph) |
| 229 | 4-$(CH_2)_9CH_3$ | 4-$CH_2Ph$ | 4-$CH_2$(2,4-di-Cl,5-$CF_3$-Ph) | 4-(2,4-di-Cl,5-$CF_3$-Ph) |
| 230 | 5-$(CH_2)_{11}CH_3$ | 5-Ph | 5-$CH_2$(2-Cl,5-$CO_2Me$-Ph) | 5-(2-Cl,5-$CO_2Me$-Ph) |
| 231 | 4-$(CH_2)_{11}CH_3$ | 4-Ph | 4-$CH_2$(2-Cl,5-$CO_2Me$-Ph) | 4-(2-Cl,5-$CO_2Me$-Ph) |
| 232 | 5-$(CH_2)_{13}CH_3$ | 5-O-cyclohexyl | 5-$CH_2$(2,4-di-Cl,5-OMe-Ph) | 5-(2,4-di-Cl,5-OMe-Ph) |
| 233 | 4-$(CH_2)_{13}CH_3$ | 4-O-cyclohexyl | 4-$CH_2$(2,4-di-Cl,5-OMe-Ph) | 4-(2,4-di-Cl,5-OMe-Ph) |

T = T-13, $R^2$ = F, Z = O, $R^3$ =

| 234 | 5-$CF_3$ | 5-$C(CH_3)_3$ | 5-$CH_2$(4-Cl-Ph) | 5-(4-Cl-Ph) |
|---|---|---|---|---|
| 235 | 5-Br | 5-$O(CH_2)_9CH_3$ | 5-$CH_2$(4-$CF_3$-Ph) | 5-(4-$CF_3$-Ph) |
| 236 | 5-$(CH_2)_4CH_3$ | 5-OPh | 5-$CH_2$(3-$CF_3$-Ph) | 5-(3-$CF_3$-Ph) |
| 237 | 5-$(CH_2)_5CH_3$ | 5-$OCH_2Ph$ | 5-$CH_2$(2,4-di-Cl-Ph) | 5-(2,4-di-Cl-Ph) |
| 238 | 5-$(CH_2)_6CH_3$ | 5-Pyr | 5-$CH_2$(2,5-di-Cl-Ph) | 5-(2,5-di-Cl-Ph) |
| 239 | 5-$(CH_2)_7CH_3$ | 5-$CH_2Pyr$ | 5-$CH_2$(3-Cl,4-F-Ph) | 5-(3-Cl,4-F-Ph) |
| 240 | 5-$(CH_2)_8CH_3$ | 5-O-Pyr | 5-$CH_2$(2-Cl,4-$CF_3$-Ph) | 5-(2-Cl,4-$CF_3$-Ph) |
| 241 | 5-$(CH_2)_9CH_3$ | 5-$CH_2Ph$ | 5-$CH_2$(2-F,5-OMe-Ph) | 5-(2-F,5-OMe-Ph) |
| 242 | 5-$CH(CH_3)_2$ | 5-Ph | 5-$CH_2$(2,4,5-tri-Cl-Ph) | 5-(2,4,5-tri-Cl-Ph) |
| 243 | 5-cyclohexyl | 5-O-cyclohexyl | 5-$CH_2$(2,4-di-Cl,5-$CF_3$-Ph) | 5-(2,4-di-Cl,5-$CF_3$-Ph) |
| 244 | 5-$O(CH_2)_7CH_3$ | 5-$O(CH_2)_{11}CH_3$ | 5-$CH_2$(2,4-di-Cl,5-OMe-Ph) | 5-(2,4-di-Cl,5-OMe-Ph) |

TABLE 14

T = T-14, $R^3$ =

|  | 1 | 2 | 3 | 4 |
|---|---|---|---|---|
| 245 | 5-$CF_3$ | 5-C—$(CH_3)_3$ | 5-$CH_2$(4,-Cl-Ph) | 5-(4-Cl-Ph) |
| 246 | 5-Br | 5-$O(CH_2)_9CH_3$ | 5-$CH_2$(4-$CF_3$-Ph) | 5-(4-$CF_3$-Ph) |
| 247 | 5-$(CH_2)_4CH_3$ | 5-OPh | 5-$CH_2$(8-$CF_3$-Ph) | 5-(3-$CF_3Ph$) |

TABLE 14-continued

| | T = T-14, $R^3$ = | | |
|---|---|---|---|
| 1 | 2 | 3 | 4 |
| 248 5-$(CH_2)_5CH_3$ | 5-$OCH_2Ph$ | 5-$CH_2$(2,4-di-Cl-Ph) | 5-(2,4-di-Cl-Ph) |
| 249 5-$(CH_2)_6CH_3$ | 5-Pyr | 5-$CH_2$(2,5-di-Cl-Ph) | 5-(2,5-di-Cl-Ph) |
| 250 5-$(CH_2)_7CH_3$ | 5-$CH_2Pyr$ | 5-$CH_2$(3-Cl,4-F-Ph) | 5-(3-Cl,4-F-Ph) |
| 251 5-$(CH_2)_8CH_3$ | 5-O-Pyr | 5-$CH_2$(2-Cl,4-$CF_3$-Ph) | 5-(2-Cl,4-$CF_3$-Ph) |
| 252 5-$(CH_2)_9CH_3$ | 5-$CH_2Ph$ | 5-$CH_2$(2-F,5-OMe-Ph) | 5-(2-F,5-OMe-Ph) |
| 253 5-$CH(CH_3)_2$ | 5-Ph | 5-$CH_2$(2,4,5-tri-Cl-Ph) | 5-(2,4,5-tri-Cl-Ph) |
| 254 5-cyclohexyl | 5-O-cyclohexyl | 5-$CH_2$(2,4-di-Cl,5-$CF_3$-Ph) | 5-(2,4-di-Cl,5-$CF_3$-Ph) |
| 255 5-$O(CH_2)_7CH_3$ | 5-$O(CH_2)_{11}CH_3$ | 5-$CH_2$(2,4-di-Cl,5-OMe-Ph) | 5-(2,4-di-Cl,5-OMe-Ph) |

TABLE 15

| | T = T-15, $R^3$ = | | |
|---|---|---|---|
| 1 | 2 | 3 | 4 |
| 256 5-$CF_3$ | 5-C—$(CH_3)_3$ | 5-$CH_2$(4,-Cl-Ph) | 5-(4-Cl-Ph) |
| 257 5-Br | 5-$O(CH_2)_9CH_3$ | 5-$CH_2$(4-$CF_3$-Ph) | 5-(4-$CF_3$-Ph) |
| 258 5-$(CH_2)_4CH_3$ | 5-OPh | 5-$CH_2$(3-$CF_3$-Ph) | 5-(3-$CF_3$-Ph) |
| 259 5-$(CH_2)_5CH_3$ | 5-$OCH_2Ph$ | 5-$CH_2$(2,4-di-Cl-Ph) | 5-(2,4-di-Cl-Ph) |
| 260 5-$(CH_2)_6CH_3$ | 5-Pyr | 5-$CH_2$(2,5-di-Cl-Ph) | 5-(2,5-di-Cl-Ph) |
| 261 5-$(CH_2)_7CH_3$ | 5-$CH_2Pyr$ | 5-$CH_2$(3-Cl,4-F-Ph) | 5-(3-Cl,4-F-Ph) |
| 262 5-$(CH_2)_8CH_3$ | 5-O-Pyr | 5-$CH_2$(2-Cl,4-$CF_3$-Ph) | 5-(2-Cl,4-$CF_3$-Ph) |
| 263 5-$(CH_2)_9CH_3$ | 5-$CH_2Ph$ | 5-$CH_2$(2-F,5-OMe-Ph) | 5-(2-F,5-OMe-Ph) |
| 264 5-$CH(CH_3)_2$ | 5-Ph | 5-$CH_2$(2,4,5-tri-Cl-Ph) | 5-(2,4,5-tri-Cl-Ph) |
| 265 5-cyclohexyl | 5-O-cyclohexyl | 5-CH-(2,4-di-Cl,5-$CF_3$-Ph) | 5-(2,4-di-Cl,5-$CF_3$-Ph) |
| 266 5-$O(CH_2)_7CH_3$ | 5-$O(CH_2)_{11}CH_3$ | 5-$CH_2$(2,4-di-Cl,5-OMe-Ph) | 5-(2,4-di-Cl,5-OMe-Ph) |

TABLE 16

| | T = T-16, $R^3$ = | | |
|---|---|---|---|
| 1 | 2 | 3 | 4 |
| 267 5-$CF_3$ | 5-C—$(CH_3)_3$ | 5-$CH_2$(4,-Cl-Ph) | 5-(4-Cl-Ph) |
| 268 5-Br | 5-$O(CH_2)_9CH_3$ | 5-$CH_2$(4-$CF_3$-Ph) | 5-(4-$CF_3$-Ph) |
| 269 5-$(CH_2)_4CH_3$ | 5-OPh | 5-$CH_2$(3-$CF_3$-Ph) | 5-(3-$CF_3$-Ph) |
| 270 5-$(CH_2)_5CH_3$ | 5-$OCH_2Ph$ | 5-$CH_2$(2,4-di-Cl-Ph) | 5-(2,4-di-Cl-Ph) |
| 271 5-$(CH_2)_6CH_3$ | 5-Pyr | 5-$CH_2$(2,5-di-Cl-Ph) | 5-(2,5-di-Cl-Ph) |
| 272 5-$(CH_2)_7CH_3$ | 5-$CH_2Pyr$ | 5-$CH_2$(3-Cl,4-F-Ph) | 5-(3-Cl,4-F-Ph) |
| 273 5-$(CH_2)_8CH_3$ | 5-O-Pyr | 5-$CH_2$(2-Cl,4-$CF_3$-Ph) | 5-(2-Cl,4-$CF_3$-Ph) |
| 274 5-$(CH_2)_9CH_3$ | 5-$CH_2Ph$ | 5-$CH_2$(2-F,5-OMe-Ph) | 5-(2-F,5-OMe-Ph) |
| 275 5-$CH(CH_3)_2$ | 5-Ph | 5-$CH_2$(2,4,5-tri-Cl-Ph) | 5-(2,4,5-tri-Cl-Ph) |
| 276 5-cyclohexyl | 5-O-cyclohexyl | 5-$CH_2$(2,4-di-Cl,5-$CF_3$-Ph) | 5-(2,4-di-Cl,5-$CF_3$-Ph) |
| 277 5-$O(CH_2)_7CH_3$ | 5-$O(CH_2)_{11}CH_3$ | 5-$CH_2$(2,4-di-Cl,5-OMe-Ph) | 5-(2,4-di-Cl,5-OMe-Ph) |

TABLE 17

| | T = T-17, $R^3$ = | | |
|---|---|---|---|
| 1 | 2 | 3 | 4 |
| 278 5-$CF_3$ | 5-C—$(CH_3)_3$ | 5-$CH_2$(4,-Cl-Ph) | 5-(4-Cl-Ph) |
| 279 5-Br | 5-$O(CH_2)_9CH_3$ | 5-$CH_2$(4-$CF_3$-Ph) | 5-(4-$CF_3$-Ph) |
| 280 5-$(CH_2)_4CH_3$ | 5-OPh | 5-$CH_2$(3-$CF_3$-Ph) | 5-(3-$CF_3$-Ph) |
| 281 5-$(CH_2)_5CH_3$ | 5-$OCH_2Ph$ | 5-$CH_2$(2,4-di-Cl-Ph) | 5-(2,4-di-Cl-Ph) |
| 282 5-$(CH_2)_6CH_3$ | 5-Pyr | 5-$CH_2$(2,5-di-Cl-Ph) | 5-(2,5-di-Cl-Ph) |
| 283 5-$(CH_2)_7CH_3$ | 5-$CH_2Pyr$ | 5-$CH_2$(3-Cl,4-F-Ph) | 5-(3-Cl,4-F-Ph) |
| 284 5-$(CH_2)_8CH_3$ | 5-O-Pyr | 5-$CH_2$(2-Cl,4-$CF_3$-Ph) | 5-(2-Cl,4-$CF_3$-Ph) |
| 285 5-$(CH_2)_9CH_3$ | 5-$CH_2Ph$ | 5-$CH_2$(2-F,5-OMe-Ph) | 5-(2-F,5-OMe-Ph) |
| 286 5-$CH(CH_3)_2$ | 5-Ph | 5-$CH_2$(2,4,5-tri-Cl-Ph) | 5-(2,4,5-tri-Cl-Ph) |
| 287 5-cyclohexyl | 5-O-cyclohexyl | 5-$CH_2$(2,4-di-Cl,5-$CF_3$-Ph) | 5-(2,4-di-Cl,5-$CF_3$-Ph) |
| 288 5-$O(CH_2)_7CH_3$ | 5-$O(CH_2)_{11}CH_3$ | 5-$CH_2$(2,4-di-Cl,5-OMe-Ph) | 5-(2,4-di-Cl,5-OMe-Ph) |

TABLE 18

T = T-18, $R^3$ =

| | 1 | 2 | 3 | 4 |
|---|---|---|---|---|
| 289 | 5-CF$_3$ | 5-C—(CH$_3$) | 5-CH$_2$(4,-Cl-Ph) | (4-Cl-Ph) |
| 290 | 5-Br | 5-O(CH$_2$)$_9$CH$_3$ | 5-CH$_2$(4-CF$_3$-Ph) | 5-(4-CF$_3$-Ph) |
| 291 | 5-(CH$_2$)$_4$CH$_3$ | 5-OPh | 5-CH$_2$(3-CF$_3$-Ph) | 5-(3-CF$_3$-Ph) |
| 292 | 5-(CH$_2$)$_5$CH$_3$ | 5-OCH$_2$Ph | 5-CH$_2$(2,4-di-Cl-Ph) | 5-(2,4-di-Cl-Ph) |
| 293 | 5-(CH$_2$)$_6$CH$_3$ | 5-Pyr | 5-CH$_2$(2,5-di-Cl-Ph) | 5-(2,5-di-Cl-Ph) |
| 294 | 5-(CH$_2$)$_7$CH$_3$ | 5-CH$_2$Pyr | 5-CH$_2$(3-Cl,4-F-Ph) | 5-(3-Cl,4-F-Ph) |
| 295 | 5-(CH$_2$)$_8$CH$_3$ | 5-O-Pyr | 5-CH$_2$(2-Cl,4-CF$_3$-Ph) | 5-(2-Cl,4-CF$_3$-Ph) |
| 296 | 5-(CH$_2$)$_9$CH$_3$ | 5-CH$_2$Ph | 5-CH$_2$(2-F,5-OMe-Ph) | 5-(2-F,5-OMe-Ph) |
| 297 | 5-CH(CH$_3$)$_2$ | 5-Ph | 5-CH$_2$(2,4,5-tri-Cl-Ph) | 5-(2,4,5-tri-Cl-Ph) |
| 298 | 5-cyclohexyl | 5-O-cyclohexyl | 5-CH$_2$(2,4-di-Cl,5-CF$_3$-Ph) | 5-(2,4-di-Cl,5-CF$_3$-Ph) |
| 299 | 5-O(CH$_2$)$_7$CH$_3$ | 5-O(CH$_2$)$_{11}$CH$_3$ | 5-CH$_2$(2,4-di-Cl,5-OMe-Ph) | 5-(2,4-di-Cl,5-OMe-Ph) |

TABLE 19

T = T-19, $R^3$ =

| | 1 | 2 | 3 | 4 |
|---|---|---|---|---|
| 300 | 5-CF$_3$ | 5-C—(CH$_3$)$_3$ | 5-CH$_2$(4,-Cl-Ph) | 5-(4-Cl-Ph) |
| 301 | 5-Br | 5-O(CH$_2$)$_9$CH$_3$ | 5-CH$_2$(4-CF$_3$-Ph) | 5-(4-CF$_3$-Ph) |
| 302 | 5-(CH$_2$)$_4$CH$_3$ | 5-OPh | 5-CH$_2$(3-CF$_3$-Ph) | 5-(3-CF$_3$-Ph) |
| 303 | 5-(CH$_2$)$_5$CH$_3$ | 5-OCH$_2$Ph | 5-CH$_2$(2,4-di-Cl-Ph) | 5-(2,4-di-Cl-Ph) |
| 304 | 5-(CH$_2$)$_6$CH$_3$ | 5-Pyr | 5-CH$_2$(2,5-di-Cl-Ph) | 5-(2,5-di-Cl-Ph) |
| 305 | 5-(CH$_2$)$_7$CH$_3$ | 5-CH$_2$Pyr | 5-CH$_2$(3-Cl,4-F-Ph) | 5-(3-Cl,4-F-Ph) |
| 306 | 5-(CH$_2$)$_8$CH$_3$ | 5-O-Pyr | 5-CH$_2$(2-Cl,4-CF$_3$-Ph) | 5-(2-Cl,4-CF$_3$-Ph) |
| 307 | 5-(CH$_2$)$_9$CH$_3$ | 5-CH$_2$Ph | 5-CH$_2$(2-F,5-OMe-Ph) | 5-(2-F,5-OMe-Ph) |
| 308 | 5-CH(CH$_3$)$_2$ | 5-Ph | 5-CH$_2$(2,4,5-tri-Cl-Ph) | 5-(2,4,5-tri-Cl-Ph) |
| 309 | 5-cyclohexyl | 5-O-cyclohexyl | 5-CH$_2$(2,4-di-Cl,5-CF$_3$-Ph) | 5-(2,4-di-Cl,5-CF$_3$-Ph) |
| 310 | 5-O(CH$_2$)$_7$CH$_3$ | 5-O(CH$_2$)$_{11}$CH$_3$ | 5-CH$_2$(2,4-di-Cl,5-OMe-Ph) | 5-(2,4-di-Cl,5-OMe-Ph) |

TABLE 20

T = T-20, $R^3$ =

| | 1 | 2 | 3 | 4 |
|---|---|---|---|---|
| 311 | 5-CF$_3$ | 5-C—(CH$_3$)$_3$ | 5-CH$_2$(4,-Cl-Ph) | 5-(4-Cl-Ph) |
| 312 | 5-Br | 5-O(CH$_2$)$_9$CH$_3$ | 5-CH$_2$(4-CF$_3$-Ph) | 5-(4-CF$_3$-Ph) |
| 313 | 5-(CH$_2$)$_4$CH$_3$ | 5-OPh | 5-CH$_2$(3-CF$_3$-Ph) | 5-(3-CF$_3$-Ph) |
| 314 | 5-(CH$_2$)$_5$CH$_3$ | 5-OCH$_2$Ph | 5-CH$_2$(2,4-di-Cl-Ph) | 5-(2,4-di-Cl-Ph) |
| 315 | 5-(CH$_2$)$_6$CH$_3$ | 5-Pyr | 5-CH$_2$(2,5-di-Cl-Ph) | 5-(2,5-di-Cl-Ph) |
| 316 | 5-(CH$_2$)$_7$CH$_3$ | 5-CH$_2$Pyr | 5-CH$_2$(3-Cl,4-F-Ph) | 5-(3-Cl,4-F-Ph) |
| 317 | 5-(CH$_2$)$_8$CH$_3$ | 5-O-Pyr | 5-CH$_2$(2-Cl,4-CF$_3$-Ph) | 5-(2-Cl,4-CF$_3$-Ph) |
| 318 | 5-(CH$_2$)$_9$CH$_3$ | 5-CH$_2$Ph | 5-CH$_2$(2-F,5-OMe-Ph) | 5-(2-F,5-OMe-Ph) |
| 319 | 5-CH(CH$_3$)$_2$ | 5-Ph | 5-CH$_2$(2,4,5-tri-Cl-Ph) | 5-(2,4,5-tri-Cl-Ph) |
| 320 | 5-cyclohexyl | 5-O-cyclohexyl | 5-CH$_2$(2,4-di-Cl,5-CF$_3$-Ph) | 5-(2,4-di-Cl,5-CF$_3$-Ph) |
| 321 | 5-O(CH$_2$)$_7$CH$_3$ | 5-O(CH$_2$)$_{11}$CH$_3$ | 5-CH$_2$(2,4-di-Cl,5-OMe-Ph) | 5-(2,4-di-Cl,5-OMe-Ph) |

TABLE 21

T = T-21, $R^3$ =

| | 1 | 2 | 3 | 4 |
|---|---|---|---|---|
| 322 | 4-CF$_3$ | 5-CF$_3$ | H | 5-(CH$_2$)$_3$CH$_3$ |
| 322 | 4-Cl | 5-Cl | 5-CO$_2$Me | 5-CH$_2$CH(CH$_3$)$_2$ |
| 323 | 4-F | 5-F | 5-CO$_2$Et | 5-CH$_2$C(CH$_3$)$_3$ |
| 324 | 4-Br | 5-Br | 5-COCH$_3$ | 5-CH(CH$_3$)CH$_2$CH$_3$ |
| 325 | 4-OMe | 5-OMe | 5-CH$_3$ | 5-C(CH$_3$)$_3$ |
| 326 | 4-OEt | 5-OEt | 5-CH$_2$CH$_3$ | 5-(CH$_2$)$_4$CH$_3$ |
| 327 | 4-OCF$_3$ | 5-OCF$_3$ | 5-CH(CH$_3$)$_2$ | 5-CH$_2$C(CH$_3$)$_3$ |
| 328 | 4-OCHF$_2$ | 5-OCHF$_2$ | 5-(CH$_2$)$_2$CH$_3$ | 5-(CH$_2$)$_2$CH(CH$_3$)$_2$ |

TABLE 22

T = T-22, $R^3$ =

| | 1 | 2 | 3 | 4 |
|---|---|---|---|---|
| 329 | 4-CF$_3$ | 5-CF$_3$ | H | 5-(CH$_2$)$_3$CH$_3$ |
| 330 | 4-Cl | 5-Cl | 5-CO$_2$Me | 5-CH$_2$CH(CH$_3$)$_2$ |
| 331 | 4-F | 5-F | 5-CO$_2$Et | 5-CH$_2$C(CH$_3$)$_3$ |
| 332 | 4-Br | 5-Br | 5-COCH$_3$ | 5-CH(CH$_3$)CH$_2$CH$_3$ |
| 333 | 4-OMe | 5-OMe | 5-CH$_3$ | 5-C(CH$_3$)$_3$ |
| 334 | 4-OEt | 5-OEt | 5-CH$_2$CH$_3$ | 5-(CH$_2$)$_4$CH$_3$ |
| 335 | 4-OCF$_3$ | 5-OCF$_3$ | 5-CH(CH$_3$)$_2$ | 5-CH$_2$C(CH$_3$)$_3$ |
| 336 | 4-OCHF$_2$ | 5-OCHF$_2$ | 5-(CH$_2$)$_2$CH$_3$ | 5-(CH$_2$)$_2$CH(CH$_3$)$_2$ |

TABLE 23

T = T-23, R³ =

| | 1 | 2 | 3 | 4 |
|---|---|---|---|---|
| 337 | 4-CF₃ | 5-CF₃ | H | 5-(CH₂)₃CH₃ |
| 338 | 4-Cl | 5-Cl | 5-CO₂Me | 5-CH₂CH(CH₃)₂ |
| 339 | 4-F | 5-F | 5-CO₂Et | 5-CH₂C(CH₃)₃ |
| 340 | 4-Br | 5-Br | 5-COCH₃ | 5-CH(CH₃)CH₂CH₃ |
| 341 | 4-OMe | 5-OMe | 5-CH₃ | 5-C(CH₃)₃ |
| 342 | 4-OEt | 5-OEt | 5-CH₂CH₃ | 5-(CH₂)₄CH₃ |
| 343 | 4-OCF₃ | 5-OCF₃ | 5-CH(CH₃)₂ | 5-CH₂C(CH₃)₃ |
| 344 | 4-OCHF₂ | 5-OCHF₂ | 5-(CH₂)₂CH₃ | 5-(CH₂)₂CH(CH₃)₂ |

TABLE 25

T = T-24, R³ =

| | 2 | 3 | 4 |
|---|---|---|---|
| 345 | 4-CF₃ | 5-CF₃ | H | 5-(CH₂)₃CH₃ |
| 346 | 4-Cl | 5-Cl | 5-CO₂Me | 5-CH₂CH(CH₃)₂ |
| 347 | 4-F | 5-F | 5-CO₂Et | 5-CH₂C(CH₃)₃ |
| 348 | 4-Br | 5-Br | 5-COCH₃ | 5-CH(CH₃)CH₂CH₃ |
| 349 | 4-OMe | 5-OMe | 5-CH₃ | 5-C(CH₃)₃ |
| 350 | 4-OEt | 5-OEt | 5-CH₂CH₃ | 5-(CH₂)₄CH₃ |
| 351 | 4-OCF₃ | 5-OCF₃ | 5-CH(CH₃)₂ | 5-CH₂C(CH₃)₃ |
| 352 | 4-OCHF₂ | 5-OCHF₂ | 5-(CH₂)₂CH₃ | 5-(CH₂)₂CH(CH₃)₂ |

TABLE 25

T = T-25, R³ =

| | 1 | 2 | 3 | 4 |
|---|---|---|---|---|
| 353 | 4-CF₃ | 5-CF₃ | H | 5-(CH₂)₃CH₃ |
| 354 | 4-Cl | 5-Cl | 5-CO₂Me | 5-CH₂CH(CH₃)₂ |
| 355 | 4-F | 5-F | 5-CO₂Et | 5-CH₂C(CH₃)₃ |
| 356 | 4-Br | 5-Br | 5-COCH₃ | 5-CH(CH₃)CH₂CH₃ |
| 357 | 4-OMe | 5-OMe | 5-CH₃ | 5-C(CH₃)₃ |
| 358 | 4-OEt | 5-OEt | 5-CH₂CH₃ | 5-(CH₂)₄CH₃ |
| 359 | 4-OCF₃ | 5-OCF₃ | 5-CH(CH₃)₂ | 5-CH₂C(CH₃)₃ |
| 360 | 4-OCHF₂ | 5-OCHF₂ | 5-(CH₂)₂CH₃ | 5-(CH₂)₂CH(CH₃)₂ |

TABLE 26

T = T-26, R³ =

| | 1 | 2 | 3 | 4 |
|---|---|---|---|---|
| 361 | 4-CF₃ | 5-CF₃ | H | 5-(CH₂)₃CH₃ |
| 362 | 4-Cl | 5-Cl | 5-CO₂Me | 5-CH₂CH(CH₃)₂ |
| 363 | 4-F | 5-F | 5-CO₂Et | 5-CH₂C(CH₃)₃ |
| 364 | 4-Br | 5-Br | 5-COCH₃ | 5-CH(CH₃)CH₂CH₃ |
| 365 | 4-OMe | 5-OMe | 5-CH₃ | 5-C(CH₃)₃ |
| 366 | 4-OEt | 5-OEt | 5-CH₂CH₃ | 5-(CH₂)₄CH₃ |
| 367 | 4-OCF₃ | 5-OCF₃ | 5-CH(CH₃)₂ | 5-CH₂C(CH₃)₃ |
| 368 | 4-OCHF₂ | 5-OCHF₂ | 5-(CH₂)₂CH₃ | 5-(CH₂)₂CH(CH₃)₂ |

TABLE 27

T = T-27, R³ =

| | 1 | 2 | 3 | 4 |
|---|---|---|---|---|
| 369 | 2-CF₃ | H | 2-CH₃ | 2-CH₂C(CH₃)₃ |
| 370 | 2-Cl | 2-OCF₃ | 2-CH₂CH₃ | 2-CH(CH₃)CH₂CH₃ |
| 371 | 2-F | 2-OCHF₂ | 2-(CH₂)₂CH₃ | 2-C(CH₃)₃ |
| 372 | 2-Br | 2-CO₂Me | 2-CH(CH₃)₂ | 2-(CH₂)₄CH₃ |
| 373 | 2-OMe | 2-CO₂Et | 2-(CH₂)₃CH₃ | 2-CH₂C(CH₃)₃ |
| 374 | 2-OEt | 2-COCH₃ | 2-CH₂CH(CH₃)₂ | 2-(CH₂)₂CH(CH₃)₂ |

TABLE 28

T = T-28, R³ =

| | 1 | 2 | 3 | 4 |
|---|---|---|---|---|
| 375 | 2-CF₃ | H | 2-CH₃ | 2-CH₂C(CH₃)₃ |
| 376 | 2-Cl | 2-OCF₃ | 2-CH₂CH₃ | 2-CH(CH₃)CH₂CH₃ |
| 377 | 2-F | 2-OCHF₂ | 2-(CH₂)₂CH₃ | 2-C(CH₃)₃ |
| 378 | 2-Br | 2-CO₂Me | 2-CH(CH₃)₂ | 2-(CH₂)₄CH₃ |
| 379 | 2-OMe | 2-CO₂Et | 2-(CH₂)₃CH₃ | 2-CH₂C(CH₃)₃ |
| 380 | 2-OEt | 2-COCH₃ | 2-CH₂CH(CH₃)₂ | 2-(CH₂)₂CH(CH₃)₂ |

TABLE 29

T = T-29, $R^3$ =

| | 1 | 2 | 3 | 4 |
|---|---|---|---|---|
| 381 | 2-$CF_3$ | H | 2-$CH_3$ | 2-$CH_2C(CH_3)_3$ |
| 382 | 2-Cl | 2-$OCF_3$ | 2-$CH_2CH_3$ | 2-$CH(CH_3)CH_2CH_3$ |
| 383 | 2-F | 2-$OCHF_2$ | 2-$(CH_2)_2CH_3$ | 2-$C(CH_3)_3$ |
| 384 | 2-Br | 2-$CO_2Me$ | 2-$CH(CH_3)_2$ | 2-$(CH_2)_4CH_3$ |
| 385 | 2-OMe | 2-$CO_2Et$ | 2-$(CH_2)_3CH_3$ | 2-$CH_2C(CH_3)_3$ |
| 386 | 2-OEt | 2-$COCH_3$ | 2-$CH_2CH(CH_3)_2$ | 2-$(CH_2)_2CH(CH_3)_2$ |

TABLE 30

T = T-30, $R^3$ =

| | 1 | 2 | 3 | 4 |
|---|---|---|---|---|
| 387 | 2-$CF_3$ | H | 2-$CH_3$ | 2-$CH_2C(CH_3)_3$ |
| 388 | 2-Cl | 2-$OCF_3$ | 2-$CH_2CH_3$ | 2-$CH(CH_3)CH_2CH_3$ |
| 389 | 2-F | 2-$OCHF_2$ | 2-$(CH_2)_2CH_3$ | 2-$C(CH_3)_3$ |
| 390 | 2-Br | 2-$CO_2Me$ | 2-$CH(CH_3)_2$ | 2-$(CH_2)_4CH_3$ |
| 391 | 2-OMe | 2-$CO_2Et$ | 2-$(CH_2)_3CH_3$ | 2-$CH_2C(CH_3)_3$ |
| 392 | 2-OEt | 2-$COCH_3$ | 2-$CH_2CH(CH_3)_2$ | 2-$(CH_2)_2CH(CH_3)_2$ |

TABLE 31

T = T-31, G = O, m = 1 or 2, $R^6$ =

| | 1 | 2 | 3 | 4 |
|---|---|---|---|---|
| 393 | 6-H | 6,6-diMe | 6,6-diEt | 6-Me,6-Et |
| 394 | 7,7-diMe | 8,8-diMe | 6-Me | 6-nBu |
| 395 | 6-H | 6,6-diMe | 6,6-diEt | 6-Me,6-Et |
| 396 | 7,7-diMe | 8,8-diMe | 6-Me | 6-nBu |
| 397 | 6-H | 6,6-diMe | 6,6-diEt | 6-Me,6-Et |
| 398 | 7,7-diMe | 8,8-diMe | 6-Me | 6-nBu |

TABLE 32

T = T-32, G = O, m = 1 or 2, $R^6$ =

| | 1 | 2 | 3 | 4 |
|---|---|---|---|---|
| 399 | 5-H | 5,5-diMe | 5,5-diEt | 5-Me,5-Et |
| 400 | 5-H | 5,5-diMe | 5,5-diEt | 5-Me,5-Et |

TABLE 33

T = T-33, G = O, m = 1 or 2, $R^6$ =

| | 1 | 2 | 3 | 4 |
|---|---|---|---|---|
| 401 | 5-H | 5,5-diMe | 5,5-diEt | 5-Me,5-Et |
| 402 | 5-H | 5,5-diMe | 5,5-diEt | 5-Me,5-Et |

Formulation/Utility

Compounds of this invention will generally be used in formulation with an agriculturally suitable carrier comprising a liquid or solid diluent. Useful formulations include dusts, granules, baits, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 5–90 | 0–74 | 1–10 |
| Oil Suspensions, Emulsions Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents and solvents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth, and the like.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations*, Washington, D.C., 1988, pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, Dec. 4, 1967, pp 147–148, *Perry's Chemical Engineer's*

*Handbook*, 4th Ed., McGraw-Hill, New York, 1963, pages 8–57 and following, and WO 91/13546.

For further information regarding the art of formulation, see U.S. Pat. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138 –140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

Example A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| Compound 1 | 10.0% |
| attapulgite granules (low volatile matter, 0.71/0.30 mm; U.S.S. No. 25–50 sieves) | 90.0%. |

Example C

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

Emulsifiable Concentrate

| | |
|---|---|
| Compound 1 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, stem or root feeding, seed-feeding, aquatic and soil-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all growth stages of all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders. Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, juveniles and adults of the Phylum Nematoda. The compounds of this invention are also active against pests of the Orders Hymenoptera, Isoptera, Siphonaptera, Blattaria, Thysanura and Psocoptera; pests belonging to the Class Arachnida and Phylum Platyhelminthes. Specifically, the compounds are active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphisfabae*), tobacco budworm (*Heliothis virescens*), rice water weevil (*Lissorhoptrus oryzophilus*), rice leaf beetle (*Oulema oryzae*), whitebacked planthopper (*Sogatellafurcifera*), green leafhopper (*Nephotettix cincticeps*), brown planthopper (*Nilaparvata lugens*), small brown planthopper (*Laodelphax striatellus*), rice stem borer (*Chilo sugpressalis*), rice leafroller (*Cnaphalocrocis medinalis*), black rice stink bug (*Scotinophara lurida*), rice stink bug (*Oebalus pugnax*), rice bug (*Leptocorisa chinensis*), slender rice bug (*Cletus puntiger*), and southern green stink bug (*Nezara viridula*). The compounds are active on mites, demonstrating ovicidal, larvicidal and chemosterilant activity against such families as Tetranychidae including *Tetranychus urticae*, *Tetranychus cinnabarinus*, *Tetranychus mcdanieli*, *Tetranychus pacificus*, *Tetranychus turkestani*, *Byrobia rubrioculus*, *Panonychus ulmi*, *Panonychus citri*, *Eotetranychus carpini borealis*, *Eotetranychus*, *hicoriae*, *Eotetranychus sexrnaculatus*, *Eotetranychus yumensis*, *Eotetranychus banksi* and *Oligonychus pratensis;* Tenuipalpidae including *Brevipalpus lewisi*, *Brevipalpus phoenicis*, *Brevipalpus californicus* and *Brevipalpus obovatus;* Eriophyidae including *Phyllocoptruta oleivora*, *Eriophyes sheldoni*, *Aculus cornutus*, *Epitrimerus pyri* and *Eriophyes mangiferae*. See WO 90/10623 and WO 92/00673 for more detailed pest descriptions.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of other agricultural protectants with which compounds of this invention can be formulated are: insecticides such as avermectin B, monocrotophos, carbofuran, tetrachlorvinphos, malathion, parathion-methyl, methomyl, chlordimeform, diazinon, deltamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, metha-midophos, phosmet, phosphamidon, phosalone, pirimicarb, phorate, terbufos, trichlorfon, methoxychlor, bifenthrin, biphenate, cyfluthrin, tefluthrin, fenpropathrin, fluvalinate, flucythrinate, tralomethrin, imidacloprid, metaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-Al, chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neoasozin, pencycuron, probenazole, pyroquilon, tricyclazole, validamycin, and flutolanil; nematocides such as aldoxycarb, fenamiphos and fosthietan; bactericides such as oxytetracycline, streptomycin and tribasic copper sulfate; acaricides such as binapacryl, oxythioquinox, chlorobenzilate, dicofol, dienochlor, cyhexatin, hexythiazox, amitraz, propargite, tebufenpyrad and fenbutatin oxide; and biological agents such as entomopathogenic bacteria, virus and fungi.

In certain instances, combinations with other arthropodicides having a similar spectrum of control but a different mode of action will be particularly advantageous for resistance management.

Arthropod pests are controlled and protection of agronomic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of Formula I, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, baits, eartags, boluses, foggers, fumigants, aerosols, dusts and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, and synergists and other solvents such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following TESTS demonstrate the control efficacy of compounds of this invention on specific pests. The pest control protection afforded by the compounds is not limited, however, to these species. See Index Table A for compound descriptions.

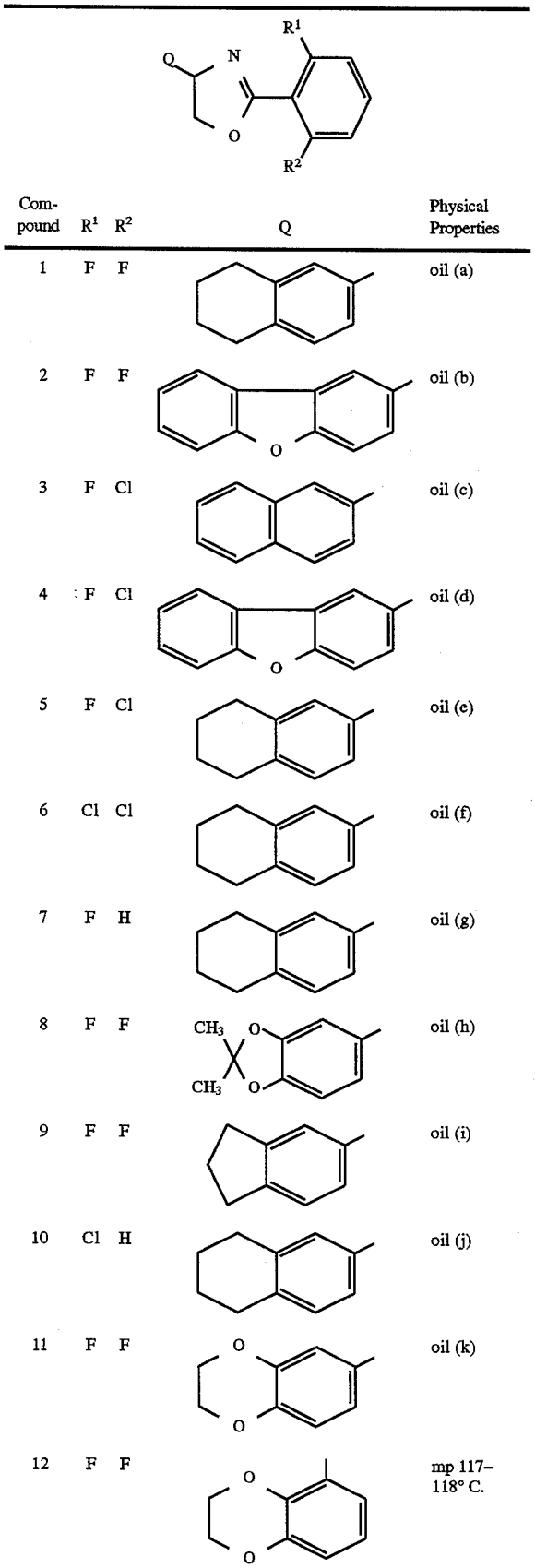

INDEX TABLE A-continued

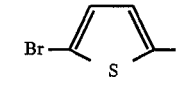

| Compound | R¹ | R² | Q | Physical Properties |
|---|---|---|---|---|
| 13 | F | F | Br-thiophene | oil (l) |
| 14 | F | F | phenyl-thiophene | oil (m) |
| 15 | F | F | 3-CF₃-phenyl-thiophene | oil (n) |
| 16 | F | F | 2,4-diCl-phenyl-thiophene | oil (o) |
| 17 | F | F | 3-Cl-4-F-phenyl-thiophene | oil (p) |
| 18 | F | F | 3,5-diCl-phenyl-thiophene | oil (q) |
| 19 | F | F | 4-MeO-phenyl-thiophene | oil (r) |
| 20 | F | F | naphthyl | mp 68–70° C. |
| 21 | F | F | 4-CF₃-phenyl-thiophene | mp 64–58° C.: |
| 22 | F | F | 4-Br-phenyl-thiophene | semi-solid (s) |
| 23 | F | F | 4-Cl-phenyl-thiophene | mp 96–98° C. |

INDEX TABLE A-continued

| Compound | R¹ | R² | Q | Physical Properties |
|---|---|---|---|---|
| 24 | F | F | 4-F-phenyl-thiophene | oil (t) |
| 25 | F | F | benzyl-thiophene | oil (u) |
| 26 | F | F | CH₃(CH₂)₇-thiophene | oil (v) |
| 27 | F | F | t-Bu-thiophene | oil (w) |
| 28 | F | Cl | 4-Cl-phenyl-thiophene | mp 117–118° C. |
| 29 | Cl | Cl | 4-Cl-phenyl-thiophene | mp 125–127° C. |
| 30 | F | F | thiophene | oil (x) |
| 31 | F | F | methylenedioxyphenyl | mp 88–90° C. |
| 32 | F | F | 2,2-dimethylchroman | mp 75–76° C. |

¹H NMR data for compounds in Table A (CDCl₃, 200 MHz, δ)
(a) 7.4–7.0 (6H), 5.4 (1H), 4.8 (1H), 4.3 (1H), 2.8 (4H), 1.8 (4H)
(b) 8.0–7.1 (10H), 5.6 (1H), 4.9 (1H), 4.4 (1H)
(c) 8.0–7.0 (10H), 5.65 (1H), 4.9 (1H), 4.4 (1H)
(d) 8.0–7.1 (10H), 5.65 (1H), 4.9.(1H), 4.4 (1H)
(e) 7.4–7.0 (6H), 5.4 (1H), 4.8 (1H), 4.3 (1H), 2.8 (4H), 1.8 (4H)
(f) 7.4–7.1 (6H), 5.5 (1H), 4.8 (1H), 4.3 (1H), 2.8 (4H), 1.8 (4H)
(g) 8.0–7.1 (7H), 5.4 (1H), 4.8 (1H), 4.3 (1H), 2.8 (4H), 1.8 (4H)
(h) 7.3–6.7 (6H), 5.4 (1H), 4.8 (1H), 4.3 (1H), 1.6 (6H)
(i) 7.4–7.0 (6H) 3 5.4 (1H), 4.8 (1H), 4.1 (1H), 2.9 (4H), 2.0 (2H)
(j) 8.0–7.0 (7H), 5.4 (1 H), 4.8 (1H), 4.3 (1H), 2.8 (4H), 1.8 (4H)
(k) 7.4–6.8 (6H), 5.4 (1H), 4.8 (1H), 4.3 (1H), 4.2 (4H)
(l) 7.70 (1H), 7.30 (2H), 7.15 (1H), 6.95 (1H), 5.70 (1H), 4.80 (1H), 4.35 (1H)
(m) 7.20–6.90 (10H), 5.70 (1H), 4.80 (1H), 4.45 (1H)
(n) 7.79 (2H), 7.45 (2H), 7.25 (1H), 7.10 (3H), 5.70 (1H), 4.82 (1H), 4.45 (1H)

INDEX TABLE A-continued

[Structure with R¹, R², Q, N, O]

| Compound | R¹ | R² | Q | Physical Properties |
|---|---|---|---|---|

(o) 7.46 (3H), 7.25 (2H), 7.00 (3H), 5.70 (1H), 4.81 (1H), 4.40 (1H)
(p) 7.61 (1H), 7.44 (2H), 7.13 (2H), 7.00 (3H), 5.70 (1H), 4.82 (1H), 4.40 (1H)
(q) 7.43 (3H), 7.24 (2H), 6.99 (3H), 5.70 (1H), 4.82 (1H), 4.30 (1H)
(r) 7.50 (2H), 7.41 (1H), 7.08 (1H), 6.98 (3H), 6.90 (2H), 5.70 (1H), 4.81 (1H), 4.85 (1H), 3.83 (3H)
(s) 7.64–6.99 (9H), 5.70 (1H), 4.82 (1H), 4.43 (1H)
(t) 7.58–6.98 (9H), 5.69 (1H), 4.80 (1H), 4.42 (1H)
(u) 7.41–6.60 (10H), 5.60 (1H), 4.75 (1H), 4.34 (1H), 4.10 (2H)
(v) 7.40–6.64 (5H), 5.62 (1H), 4.76 (1H), 4.40 (1H), 2.76 (2H), 1.68 (2H), 1.20 (10H), 0.86 (3H)
(w) 7.21–6.70 (5H), 5.65 (1H), 4.78 (1H), 4.41 (1H), 1.36 (9H)
(x) 7.42–6.95 (6H), 5.72 (1H), 4.80 (1H), 4.41 (1H)

TEST A

Two-Spotted Spider Mite (*Tetranychus urticae*)

A solution of the test compound was prepared by dissolving it in a minimum of acetone and then adding water containing a wetting agent until the concentration of Compound 1 was 50 ppm. Two-week old red kidney bean plants infested with two-spotted spider mites eggs were sprayed to run-off with the test solution using a turntable sprayer. Plants were held in a chamber at 25° C. and 50% relative humidity. Of the compounds tested, the following gave mortality levels of 80% or higher seven days after spraying: 1, 2*, 3*, 4*, 5, 6, 7, 8, 9, 11, 12, 13, 14, 15, 16, 17, 18, 20*, 21, 22, 23, 24, 25, 27, 28, 29.

*test concentration was 10 ppm.

TEST B

Fall Armyworm

Test units, each consisting of a H.I.S. (high impact styrene) trays with 16 cells were prepared. In 12 of the cells, wet filter paper and approximately 8 cm² of lima leaf were placed, in the other 4 cells was placed a 0.5 cm layer of wheat germ diet. Fifteen to twenty third instar larvae of fall armyworm (*Spodoptera frugiperda*) were placed in a 8 ounce (230 mL) plastic cup. Solutions of each of the test compounds in 75/25 acetone/distilled water solvent were sprayed into the tray and cup. Spraying was accomplished by passing the tray and cup, on a conveyor belt, directly beneath a flat fan hydraulic nozzle which discharged the spray at a rate of 0.125 pounds of active ingredient per acre (about 0.137 kg/ha) at 30 psi (207 kPa). The insects were transferred into the tray (one insect per cell). The trays were covered and held at 27° C. and 50% relative humidity for 48 hours after which time readings were taken on the 12 cells with lima leaves. The 4 remaining cells were read at 7 days for a delayed toxicity reading. Of the compounds tested, the following gave mortality levels of 80% or higher at the 7 day reading: 15, 16, 17, 21, 22, 23*.

*test concentration was 1000 ppm

We claim:

1. A compound of the formula

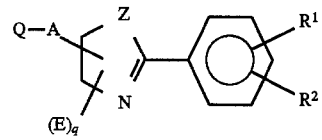

wherein:

A is selected from the group a direct bond and $C_1$–$C_3$ straight or branched chain alkylene;

E is selected from the group $C_1$–$C_4$ alkyl and $C_1$–$C_4$ haloalkyl;

Z is selected from the group O and S;

q is 0, 1, 2 or 3;

Q is a 5- to 16- membered aromatic ring system selected from the group:
  (i) monocylic aromatic ring containing 1 to 4 heteroatoms independently selected from the group 0–4 nitrogen, 0–1 oxygen, and 0–1 sulfur;
  (ii) fused carbobicyclic ring containing 8 to 12 carbons, with the proviso that when the ring is naphthyl and is on the oxazoline ring carbon adjacent to the oxazoline ring oxygen, and when E is $CH_3$ and q is 1, then $R^1$ is other than H;
  (iii) fused carbotricyclic ring containing 12 to 16 carbons;
  (iv) fused bicylic ring containing 1 to 4 heteroatoms independently selected from the group 0–4 nitrogen, 0–2 oxygen, and 0–2 sulfur;
  (v) fused tricylic ring containing 1 to 6 heteroatoms independently selected from the group 0–4 nitrogen, 0–2 oxygen, and 0–2 sulfur; and
  (vi) phenyl substituted with M-J¹;

Q being substituted with 1 to 6 substituents selected independently from the group $R^3$, $R^4$, $(R^5)$ and $(R^6)_m$;

$R^1$ and $R^2$ are independently selected from the group H, halogen, $C_1$–$C_6$ alkyl, $C_1$–$C_6$ haloalkyl, $C_1$–$C_6$ haloalkoxy, $C_1$–$C_6$ alkylthio, CN and $NO_2$;

$R^3$ and $R^5$ are independently selected from the group H, halogen, $C_1$–$C_{16}$ alkyl, $C_1$–$C_{16}$ haloalkyl, $C_3$–$C_7$ cycloalkyl, $C_4$–$C_{16}$ cycloalkylalkyl, $C_2$–$C_{16}$ alkenyl, $C_2$–$C_{16}$ haloalkenyl, $C_2$–$C_{16}$ alkynyl, $C_2$–$C_{16}$ haloalkynyl, $C_2$–$C_{16}$ alkoxyalkoxy, $OR^7$, $R^7OC(O)$—, $R^7C(O)$—, $Si(R^{13})(R^{14})R^{15}$ and M-J;

$R^4$ is selected from the group H, halogen, $C_1$–$C_6$ alkyl, $C_1$–$C_6$ alkoxy, $C_1$–$C_6$ haloalkyl and $C_1$–$C_6$ haloalkoxy;

$R^6$ is selected from the group H, halogen, $C_1$–$C_{10}$ alkyl, $C_1$–$C_6$ alkoxy, $C_1$–$C_6$ haloalkyl, $C_1$–$C_6$ haloalkoxy; and phenyl optionally substituted with $R^8$;

$R^7$ is selected from the group $C_3$–$C_7$ cycloalkyl, $C_4$–$C_7$ cycloalkylalkyl, $C_1$–$C_{16}$ alkyl, $C_1$–$C_{16}$ haloalkyl, $C_2$–$C_{16}$ alkenyl, $C_2$–$C_{16}$ haloalkenyl, $C_2$–$C_{16}$ alkynyl and $C_2$–$C_{16}$ haloalkynyl;

$R^8$ is selected from the group halogen, $C_1$–$C_6$ alkyl, $C_1$–$C_6$ alkoxy, $C_1$–$C_6$ haloalkyl, $C_1$–$C_6$ haloalkoxy and $Si(R^9)(R^{10})R^{11}$;

$R^9$, $R^{10}$ and $R^{11}$ are independently $C_1$–$C_{12}$ alkyl;

M is selected from the group a direct bond, S, O, C(=O), C(=O)O—$C_1$–$C_2$ alkylene, $C_1$–$C_4$ alkylene, O—$C_1$–$C_4$ alkylene and O—$C_2$–$C_4$ alkenylene, wherein when M is O—$C_1$–$C_4$ alkylene or O—$C_2$–$C_4$ alkenylene, the oxygen atom is attached to either ring and when M is C(=O)O—$C_1$–$C_2$, the C(=O) is attached to either ring;

47

J is selected from the group phenyl optionally substituted with independently selected substituents $(R^{12})_n$; and a 5-or 6-membered aromatic ring, attached through carbon or nitrogen, containing 1 to 4 heteroatoms independently selected from the group 0–4 nitrogen, 0–1 oxygen, and 0–1 sulfur, the ring optionally substituted with independently selected substituents $(R^{12})_n$;

$J^1$ is selected from the group a 5- membered aromatic ring, attached through carbon or nitrogen, containing 1 to 4 heteroatoms independently selected from the group 0–4 nitrogen, 0–1 oxygen, and 0–1 sulfur, and a 6-membered ring containing 2 to 4 nitrogen atoms each ring optionally substituted with independently selected substituents $(R^{12})_n$;

$R^{12}$ is selected from the group halogen, $C_1-C_6$ alkyl, $C_1-C_6$ alkoxy, $C_1-C_6$ haloalkyl, $C_1-C_6$ haloalkoxy and $Si(R^{13})(R^{14})R^{15}$;

$R^{13}$, $R^{14}$ and $R^{15}$ are independently $C_1-C_{12}$ alkyl;

m and n are integers independently selected from 1 to 4; and p is 1 or 2.

2. A compound according to claim 1 wherein:
Q is selected from the group

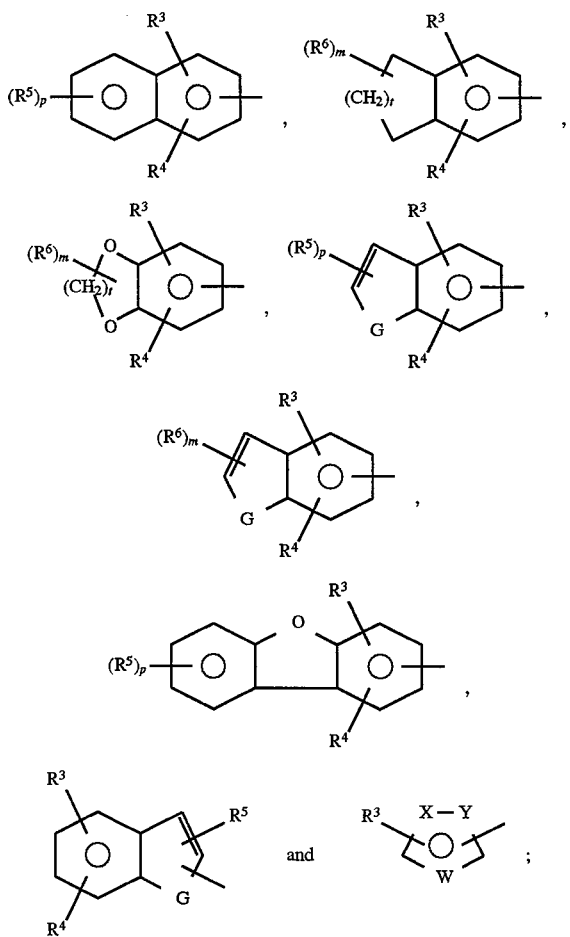

A is selected from the group a direct bond and $C_1-C_3$ straight or branched chain alkylene;

G and Z are independently selected from the group O and S;

W, X and Y are independently selected from the group S, O, $CR^3$, $N=CR^7$ and $NR^8$ wherein only one of W, X and Y can be O, S or $N=CR^7$;

48

$R^1$ and $R^2$ are independently selected from the group H, halogen, $C_1-C_6$ alkyl, $C_1-C_6$ haloalkyl, $C_1-C_6$ haloalkoxy, $C_1-C_6$ alkylthio, CN and $NO_2$;

$R^3$ and $R^5$ are independently selected from the group H, halogen, $C_1-C_{16}$ alkyl, $C_3-C_7$ cycloalkyl, $C_4-C_{16}$ cycloalkylalkyl, $C_1-C_{16}$ haloalkyl, $C_2-C_{16}$ alkenyl, $C_2-C_{16}$ haloalkenyl, $C_2-C_{16}$ alkynyl, $C_2-C_{16}$ haloalkynyl, $C_2-C_{16}$ alkoxyalkoxy, $OR^9$, $R^9OC(O)$—, $R^9C(O)$— and

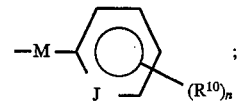

$R^4$ and $R^7$ are independently selected from the group H, halogen, $C_1-C_6$ alkyl, $C_1-C_6$ alkoxy, $C_1-C_6$ haloalkyl and $C_1-C_6$ haloalkoxy;

$R^6$ is selected from the group H, halogen, $C_1-C_{10}$ alkyl and phenyl optionally substituted with $R^{10}$;

$R^8$ is selected from the group H and $C_1-C_6$ alkyl;

$R^9$ is selected from the group $C_3-C_7$ cycloalkyl, $C_4-C_7$ cycloalkylalkyl, $C_1-C_{16}$ alkyl, $C_1-C_{16}$ haloalkyl, $C_2-C_{16}$ alkenyl, $C_2-C_{16}$ haloalkenyl, $C_2-C_{16}$ alkynyl and $C_2-C_{16}$ haloalkynyl;

$R^{10}$ is selected from the group halogen, $C_1-C_6$ alkyl, $C_1-C_6$ alkoxy, $C_1-C_6$ haloalkyl, $C_1-C_6$ haloalkoxy and $Si(R^{11})(R^{12})R^{13}$;

$R^{11}$, $R^{12}$ and $R^{13}$ are independently $C_1-C_3$ alkyl;

J is selected from the group CH, $CR^{10}$ and N;

M is selected from the group a direct bond, O, C(O), C(O)O and $C_1-C_3$ straight or branched chain alkylene;

m is an integer from 1 to 4;

n is 0 or an integer from 1 to 4;

p is 1 or 2;

t is 1, 2 or 3; and q is 0.

3. A compound according to claim 1 wherein Q is selected from the group:

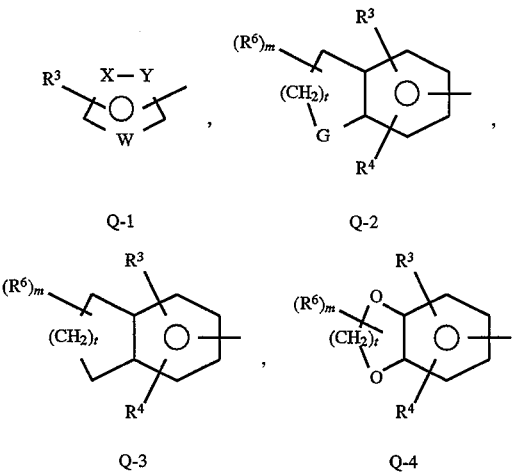

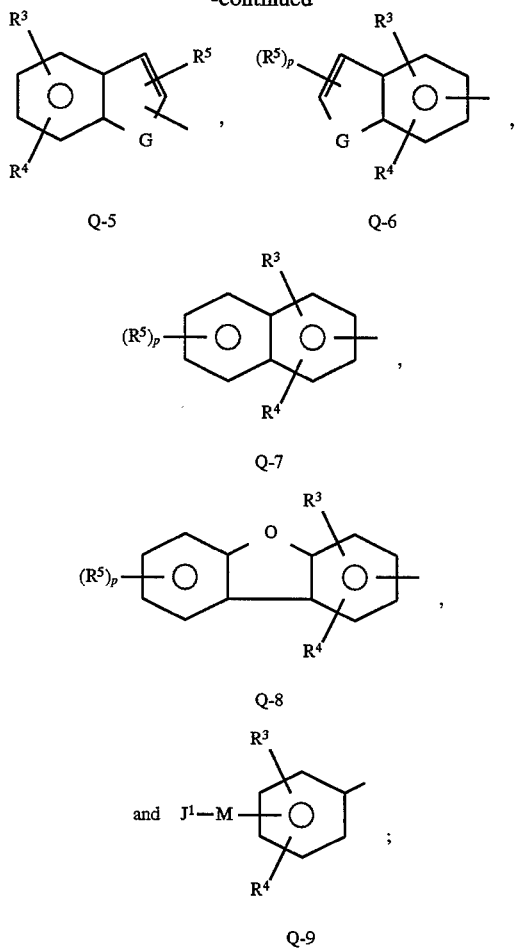

G being selected from the group O and S;

W, X and Y being independently selected from the group N, S, O, CR⁵, N=CR⁶ and NR¹⁶ wherein only one of W, X and Y is O, S or N=CR⁶;

R¹⁶ being selected from the group H, $C_1$–$C_6$ alkyl and phenyl optionally substituted with 1 to 3 substituents independently selected from the group R¹⁷;

R¹⁷ is selected from the group $C_1$–$C_3$ alkyl, $C_1$–$C_3$ haloalkyl, halogen, NO₂ and CN; and t is 1, 2 or 3.

4. A compound according to claim 3 wherein when one of W, X or Y is S, the remaining two are not both CR⁵.

5. A compound according to claim 3 wherein

A is a direct bond;

R¹ is selected from the group F and Cl in the 2-position;

R² is selected from the group H, F and Cl in the 6-position;

R³ and R⁵ are independently selected from the group H, halogen, $C_1$–$C_6$ alkyl, $C_1$–$C_6$ alkoxy, $C_1$–$C_6$ haloalkyl, $C_1$–$C_6$ haloalkoxy and M-J; and J is selected from the group phenyl, thienyl, pyridyl and furyl.

6. A compound according to claim 5 wherein Q is selected from the group Q-1, Q-2, Q-3 and Q-4.

7. A compound according to claim 6 wherein:

Q is Q-1;

W is S;

X and Y are CR⁵;

R³ is M-J;

M is a direct bond;

J is phenyl;

R¹² is in the meta or para position and is selected from the group halogen and CF₃; and n is 1 or 2.

8. A compound according to claim 6 selected from:

(2-(2,6-difluorophenyl)-4-[5-(1,1-dimethylethyl)-2-thienyl]-4,5-dihydrooxazole,

4-[5-(4-chlorophenyl)-2-thienyl]-2-2-(2,6-difluorophenyl)-4,5-dihydrooxazole, and 2-(2,6-difluorophenyl)-4-(2,2-dimethyl-1,3-benzodioxol-5-yl)-4,5-dihydrooxazole.

9. An arthropodicidal composition comprising an arthropodicidally effective amount of a compound according to any one of claims 1 to 8 and a carrier therefor.

10. A method for controlling arthropods comprising applying to the arthropods or to their environment an arthropodicidally effective amount of a compound according to any one of claims 1 to 8.

11. A method for controlling arthropods comprising applying to the arthropods or their environment an arthropodicidally effective amount of a compound of the formula

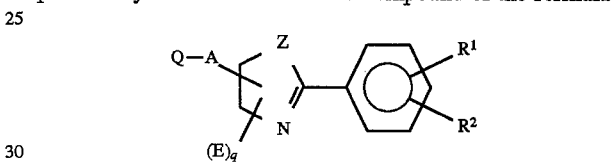

wherein:

A is selected from the group a direct bond and $C_1$–$C_3$ straight or branched chain alkylene;

E is selected from the group $C_1$–$C_4$ alkyl and $C_1$–$C_4$ haloalkyl;

Z is selected from the group O and S;

q is 0, 1, 2 or 3;

Q is a 5- to 16- membered aromatic ring system selected from the group:
 (i) monocylic aromatic ring containing 1 to 4 heteroatoms independently selected from the group 0–4 nitrogen, 0–1 oxygen, and 0–1 sulfur;
 (ii) fused carbobicyclic ring containing 8 to 12 carbons;
 (iii) fused carbotricyclic ring containing 12 to 16 carbons;
 (iv) fused bicylic ring containing 1 to 4 heteroatoms independently selected from the group 0–4 nitrogen, 0–2 oxygen, and 0–2 sulfur;
 (v) fused tricylic ring containing 1 to 6 heteroatoms independently selected from the group 0–4 nitrogen, 0–2 oxygen, and 0–2 sulfur; and
 (vi) phenyl substituted with M-J¹;

Q being substituted with 1 to 6 substituents selected independently from the group R³, R⁴, (R⁵)ₚ and (R⁶)ₘ;

R¹ and R² are independently selected from the group H, halogen, $C_1$–$C_6$ alkyl, $C_1$–$C_6$ haloalkyl, $C_1$–$C_6$ haloalkoxy, $C_1$–$C_6$ alkylthio, CN and NO₂;

R³ and R⁵ are independently selected from the group H, halogen, $C_1$–$C_{16}$ alkyl, $C_1$–$C_{16}$ haloalkyl, $C_3$–$C_7$ cycloalkyl, $C_4$–$C_{16}$ cycloalkylalkyl, $C_2$–$C_{16}$ alkenyl, $C_2$–$C_{16}$ haloalkenyl, $C_2$–$C_{16}$ alkynyl, $C_2$–$C_{16}$ haloalkynyl, $C_2$–$C_{16}$ alkoxyalkoxy, OR⁷, R⁷OC(O)—, R⁷C(O)—, Si(R¹³)(R¹⁴)R¹⁵ and M-J;

R⁴ is selected from the group H, halogen, $C_1$–$C_6$ alkyl, $C_1$–$C_6$ alkoxy, $C_1$–$C_6$ haloalkyl and $C_1$–$C_6$ haloalkoxy;

$R^6$ is selected from the group H, halogen, $C_1$–$C_{10}$ alkyl, $C_1$–$C_6$ alkoxy, $C_1$–$C_6$ haloalkyl, $C_1$–$C_6$ haloalkoxy; and phenyl optionally substituted with $R^8$;

$R^7$ is selected from the group $C_3$–$C_7$ cycloalkyl, $C_4$–$C_7$ cycloalkylalkyl, $C_1$–$C_{16}$ alkyl, $C_1$–$C_6$ haloalkyl, $C_2$–$C_{16}$ alkenyl; $C_2$–$C_{16}$ haloalkenyl, $C_2$–$C_{16}$ alkynyl and $C_2$–$C_{16}$ haloalkynyl;

$R^8$ is selected from the group halogen, $C_1$–$C_6$ alkyl, $C_1$–$C_6$ alkoxy, $C_1$–$C_6$ haloalkyl, $C_1$–$C_6$ haloalkoxy and $Si(R^9)(R^{10})R^{11}$;

$R^9$, $R^{10}$ and $R^{11}$ are independently $C_1$–$C_{12}$ alkyl;

M is selected from the group a direct bond, S, O, C(=O), C(=O)O—$C_1$–$C_2$ alkylene, $C_1$–$C_4$ alkylene, O—$C_1$–$C_4$ alkylene and O—$C_2$–$C_4$ alkenylene, wherein when M is O—$C_1$–$C_4$ alkylene or O—$C_2$–$C_4$ alkenylene, the oxygen atom is attached to either ring and when M is C(=O)O—$C_1$–$C_2$, the C(=O) is attached to either ring;

J is selected from the group phenyl optionally substituted with independently selected substituents $(R^{12})_n$; and a 5-or 6-membered aromatic ring, attached through carbon or nitrogen, containing 1 to 4 heteroatoms independently selected from the group 0–4 nitrogen, 0–1 oxygen, and 0–1 sulfur, the ring optionally substituted with independently selected substituents $(R^{12})_n$;

$J^1$ is selected from the group a 5-membered aromatic ring, attached through carbon or nitrogen, containing 1 to 4 heteroatoms independently selected from the group 0–4 nitrogen, 0–1 oxygen, and 0–1 sulfur, and a 6-membered ring containing 2 to 4 nitrogen atoms each ring optionally substituted with independently selected substituents $(R^{12})_n$;

$R^{12}$ is selected from the group halogen, $C_1$–$C_6$ alkyl, $C_1$–$C_6$ alkoxy, $C_1$–$C_6$ haloalkyl, $C_1$–$C_6$ haloalkoxy and $Si(R^{13})(R^{14})R^{15}$;

$R^{13}$, $R^{14}$ and $R^{15}$ are independently $C_1$–$C_{12}$ alkyl;

m and n are integers independently selected from 1 to 4; and p is 1 or 2.

* * * * *

UNITED STATES PATENT AND TRADEMARK OFFICE
CERTIFICATE OF CORRECTION

PATENT NO. : 5,633,271
DATED : May 27, 1997
INVENTOR(S) : Victor Ekow Amoo et al.

It is certified that error appears in the above-identified patent and that said Letters Patent is hereby corrected as shown below:

Col. 1, line 51: delete "p2"

Col. 1, line 66: delete "I" and substitute therefor --1--.

Col. 2, line 3: delete "$C_{1-C6}$" and substitute therefor --$C_1$-$C_6$--.

Col. 5, line 62: delete "4-[5-(4-chlorophenyl)-2-thienyl]-2-2-(2,6-" and substitute therefor -- 4-[5-(4-chlorophenyl)-2-thienyl]-2-(2,6- --.

Col. 46, line 36: delete "$(R^5)$" and substitute therefor --$(R^5)_p$--.

Col. 50, line 11: delete "4-[5-(4-chlorophenyl)-2-thienyl]-2-2-(2,6-" and substitute therefor -- 4-[5-(4-chlorophenyl)-2-thienyl]-2-(2,6- --.

Signed and Sealed this

Twenty-third Day of June, 1998

Attest:

BRUCE LEHMAN

*Attesting Officer*  *Commissioner of Patents and Trademarks*